United States Patent
Polejaev et al.

(10) Patent No.: US 12,357,382 B2
(45) Date of Patent: Jul. 15, 2025

(54) LASER TREATMENT USING ACOUSTIC FEEDBACK

(71) Applicant: GYRUS ACMI, INC., Westborough, MA (US)

(72) Inventors: Vladimir Polejaev, Middletown, CT (US); Sergey A. Bukesov, Acton, MA (US); Kurt G. Shelton, Bedford, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 522 days.

(21) Appl. No.: 17/378,459

(22) Filed: Jul. 16, 2021

(65) Prior Publication Data
US 2022/0022960 A1   Jan. 27, 2022

Related U.S. Application Data

(60) Provisional application No. 63/054,334, filed on Jul. 21, 2020.

(51) Int. Cl.
*A61B 18/22* (2006.01)
*A61B 1/00* (2006.01)
(Continued)

(52) U.S. Cl.
CPC .......... *A61B 18/22* (2013.01); *A61B 1/00013* (2013.01); *A61B 1/0008* (2013.01);
(Continued)

(58) Field of Classification Search
None
See application file for complete search history.

(56) References Cited

U.S. PATENT DOCUMENTS 5,825,958 A * 10/1998 Gollihar ................. A61B 18/22
                                                              385/115
5,840,023 A * 11/1998 Oraevsky ................ A61B 8/08
                                                              600/407
(Continued)

FOREIGN PATENT DOCUMENTS

CN            1050495 A     4/1991
CN           115916087 A    4/2023
(Continued)

OTHER PUBLICATIONS

"International Application Serial No. PCT/US2021/042059, International Search Report mailed Oct. 29, 2021", 5 pgs.
(Continued)

*Primary Examiner* — John P Leubecker
*Assistant Examiner* — Jae Woo
(74) *Attorney, Agent, or Firm* — Schwegman Lundberg & Woessner, P.A.

(57) ABSTRACT

Systems, devices, and methods for automatic control of laser treatment of target structure in a body of a subject based on acoustic feedback in response to delivery of laser energy to the target are disclosed. An exemplary laser energy delivery system comprises a laser system to direct laser energy at a body target, and a controller circuit to receive an acoustic signal in response to delivery of laser energy to the target, and to measure acoustic properties from the acoustic signal. The control circuit may generate control signals for controlling the laser system to adjust laser energy output, or for controlling an actuator to adjust a position of a laser fiber distal end relative to the target to achieve a desired therapeutic effect.

29 Claims, 7 Drawing Sheets

(51) Int. Cl.
*A61B 18/00* (2006.01)
*A61B 18/20* (2006.01)

(52) U.S. Cl.
CPC .............. *A61B 2018/00404* (2013.01); *A61B 2018/00577* (2013.01); *A61B 2018/00642* (2013.01); *A61B 2018/00702* (2013.01); *A61B 2018/00982* (2013.01); *A61B 2018/205547* (2017.05); *A61B 2562/0204* (2013.01)

(56) References Cited

U.S. PATENT DOCUMENTS

| | | | |
|---|---|---|---|
| 5,873,875 A * | 2/1999 | Altshuler | A61C 1/0046 606/18 |
| 6,024,703 A | 2/2000 | Zanelli et al. | |
| 6,027,492 A * | 2/2000 | Vetter | A61B 18/22 606/2 |
| 6,309,352 B1 * | 10/2001 | Oraevsky | A61F 9/00821 600/407 |
| 6,554,824 B2 | 4/2003 | Davenport et al. | |
| 9,017,316 B2 | 4/2015 | Khatchaturov et al. | |
| 9,445,871 B2 | 9/2016 | Kang et al. | |
| 9,486,286 B2 | 11/2016 | Hodel et al. | |
| 9,757,199 B2 | 9/2017 | Chia et al. | |
| 9,949,615 B2 | 4/2018 | Zappia et al. | |
| 9,968,403 B2 | 5/2018 | Hasenberg et al. | |
| 10,039,604 B2 | 8/2018 | Chia et al. | |
| 10,067,304 B2 | 9/2018 | Yu et al. | |
| 10,105,184 B2 | 10/2018 | Beck et al. | |
| 10,175,435 B2 | 1/2019 | Peng et al. | |
| 10,231,781 B2 | 3/2019 | Waisman et al. | |
| 10,258,415 B2 | 4/2019 | Harrah et al. | |
| 10,383,690 B2 | 8/2019 | Hodel et al. | |
| 2002/0013572 A1 * | 1/2002 | Berlin | A61F 2/14 606/4 |
| 2006/0122583 A1 | 6/2006 | Pesach et al. | |
| 2007/0046176 A1 * | 3/2007 | Bukesov | C09K 11/08 313/496 |
| 2007/0264625 A1 * | 11/2007 | DeBenedictis | A61B 18/22 600/315 |
| 2009/0248004 A1 * | 10/2009 | Altshuler | A61B 18/203 606/33 |
| 2012/0123399 A1 * | 5/2012 | Belikov | A61B 18/22 606/17 |
| 2014/0058244 A1 * | 2/2014 | Krocak | A61B 5/0095 600/407 |
| 2015/0224249 A1 | 8/2015 | Ciulla et al. | |
| 2015/0230864 A1 | 8/2015 | Xuan et al. | |
| 2015/0272674 A1 | 10/2015 | Xuan et al. | |
| 2016/0081749 A1 | 3/2016 | Zhang et al. | |
| 2016/0166319 A1 | 6/2016 | Yu et al. | |
| 2016/0206373 A1 | 7/2016 | Chen et al. | |
| 2016/0324424 A1 * | 11/2016 | Hengerer | G01R 33/287 |
| 2017/0014186 A1 * | 1/2017 | Chen | A61B 5/4836 |
| 2018/0092693 A1 | 4/2018 | Falkenstein et al. | |
| 2019/0113700 A1 | 4/2019 | Peng et al. | |
| 2019/0151022 A1 | 5/2019 | Yu et al. | |
| 2019/0159839 A1 | 5/2019 | Zhang et al. | |
| 2019/0192237 A1 | 6/2019 | Harrah et al. | |
| 2019/0216542 A1 * | 7/2019 | Rao | A61B 18/203 |
| 2019/0246908 A1 | 8/2019 | Pyun et al. | |
| 2019/0298449 A1 | 10/2019 | Khachaturov et al. | |
| 2019/0393669 A1 | 12/2019 | Yu et al. | |
| 2020/0000522 A1 | 1/2020 | Chia et al. | |
| 2022/0022960 A1 * | 1/2022 | Polejaev | A61B 1/00013 |
| 2022/0183563 A1 * | 6/2022 | Olivo | G01S 11/16 |
| 2022/0257319 A1 * | 8/2022 | Miernik | A61B 1/307 |

FOREIGN PATENT DOCUMENTS

| | | |
|---|---|---|
| DE | 19916653 A1 | 10/2000 |
| DE | 10257169 A1 | 7/2004 |
| EP | 3510962 A1 | 7/2019 |
| EP | 3512448 A1 | 7/2019 |
| EP | 3522811 A1 | 8/2019 |
| JP | H01308544 A | 12/1989 |
| JP | 2011507651 A | 3/2011 |
| JP | 2018516705 A | 6/2018 |
| WO | WO-9007904 A1 | 7/1990 |
| WO | WO-1990014797 A1 | 12/1990 |
| WO | WO-2020033121 A1 | 2/2020 |
| WO | WO-2022020208 A1 | 1/2022 |

OTHER PUBLICATIONS

"International Application Serial No. PCT/US2021/042059, Written Opinion mailed Oct. 29, 2021", 6 pgs.

"Indian Application Serial No. 202247074627, First Examination Report mailed Apr. 2, 2023", 5 pgs.

"International Application Serial No. PCT/US2021/042059, International Preliminary Report on Patentability mailed Feb. 2, 2023", 8 pgs.

"Indian Application Serial No. 202247074627, Response filed Oct. 2, 2023 to First Examination Report mailed Apr. 2, 2023", 28 pgs.

"Japanese Application Serial No. 2023-504389, Office Action mailed Dec. 25, 2023", w/ English Translation, 12 pgs.

"Japanese Application Serial No. 2023-504389, Response filed Mar. 7, 2024 to Office Action mailed Dec. 25, 2023", w english claims, 19 pgs.

"Japanese Application Serial No. 2023-504389, Decision of Rejection mailed Jul. 8, 2024", w/ English Translation, 8 pgs.

"Japanese Application Serial No. 2023-504389, Office Action mailed Sep. 24, 2024", w/ English Translation, 6 pgs.

"Japanese Application Serial No. 2023-504389, Response filed Aug. 28, 2024 to Decision of Rejection mailed Jul. 8, 2024", w/ current English claims, 13 pgs.

"Japanese Application Serial No. 2023-504389, Response filed Dec. 23, 2024 to Office Action mailed Sep. 24, 2024", w/ english claims, 13 pgs.

* cited by examiner

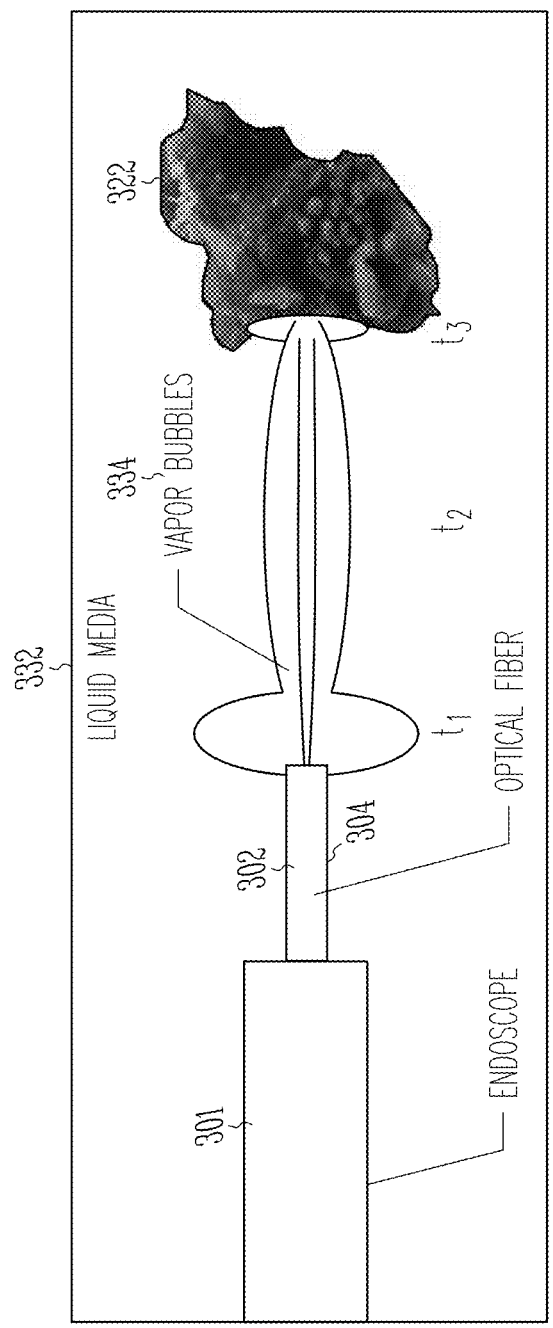
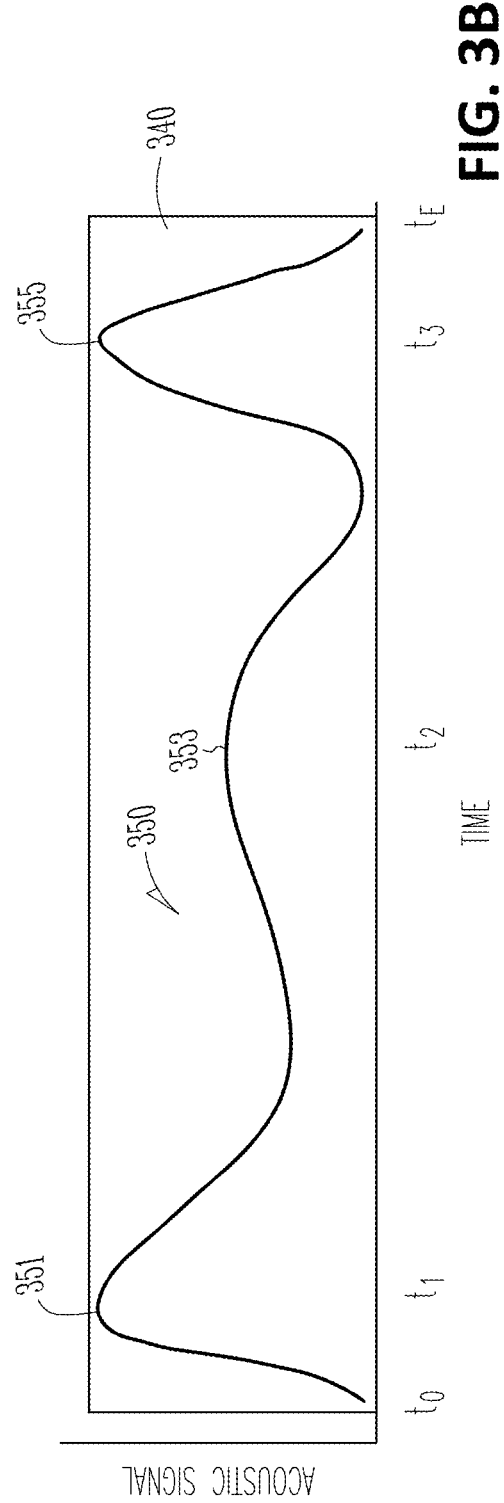
FIG. 3A
FIG. 3B

LASER TREATMENT USING ACOUSTIC FEEDBACK

CROSS-REFERENCE TO RELATED APPLICATION

This application claims the benefit of priority to U.S. Patent Application Ser. No. 63/054,334, filed Jul. 21, 2020, the contents of which are incorporated herein by reference in their entirety.

TECHNICAL FIELD

This document relates generally to a laser surgical system, and more specifically relates to a laser endoscopy system for controllably applying surgical lasers to a target using acoustic feedback.

BACKGROUND

Endoscopes are typically used to provide access to an internal location of a patient so that a doctor is provided with visual access. Some endoscopes are used in minimally invasive surgery to remove unwanted tissue or foreign objects from the body of the patient. For example, a nephroscope is used by a clinician to inspect the renal system, and to perform various procedures under direct visual control. In a percutaneous nephrolithotomy (PCNL) procedure, a nephroscope is placed through the patient's flank into the renal pelvis. Calculi or mass from various regions of a body including, for example, urinary system, gallbladder, nasal passages, gastrointestinal tract, stomach, or tonsils, can be visualized and extracted.

Laser or plasma systems have been used for delivering surgical laser energy to various target treatment areas such as soft or hard tissue. Examples of the laser treatment include ablation, coagulation, vaporization, fragmentation, etc. In lithotripsy applications, laser has been used to break down calculi structures in kidney, gallbladder, ureter, among other stone-forming regions, or to ablate large calculi into smaller fragments. In endoscopic laser treatment, it is desirable to recognize in vivo target treatment structures (e.g., calculi or cancerous tissue), such that the that lasers may be applied only to the target treatment structures and spare non-treatment tissue from unintended laser irradiation.

SUMMARY

The present document describes systems, devices, and methods for automatic control of laser treatment based on acoustic feedback in response to delivery of laser energy to the target. An exemplary endoscopic laser energy delivery system comprises a laser system to direct laser energy at a target in a body of a subject, and an acoustic feedback controller circuit to receive an acoustic signal in response to delivery of laser energy to the target, to measure one or more acoustic properties from the received acoustic signal, and to generate a first control signal for controlling the laser system to produce laser energy for delivery to the target, such as by adjusting a laser irradiation parameter setting based on the one or more acoustic properties. The control circuit may generate a second control signal to an actuator to adjust a position of a laser fiber distal end relative to the target to achieve a desired therapeutic effect.

Example 1 is a endoscopic laser energy delivery system, comprising: a laser system configured to direct laser energy at a target in a body of a subject; and an acoustic feedback controller circuit configured to: receive an acoustic signal in response to delivery of laser energy to the target; measure one or more acoustic properties from the received acoustic signal; and generate a first control signal for controlling the laser system to produce laser energy for delivery to the target based on the one or more acoustic properties.

In Example 2, the subject matter of Example 1 optionally includes the acoustic feedback controller circuit that can be configured to generate the first control signal to the laser system to adjust a laser irradiation parameter setting based on the one or more acoustic properties, and the laser system that can be configured to produce laser energy in accordance with the adjusted laser irradiation parameter setting.

In Example 3, the subject matter of any one or more of Examples 1-2 optionally include an acoustic sensor configured to sense the acoustic signal, the acoustic sensor communicatively coupled to the acoustic feedback controller circuit.

In Example 4, the subject matter of Example 3 optionally includes the acoustic sensor that can be configured to be attached to a distal portion of an endoscope.

In Example 5, the subject matter of any one or more of Examples 3-4 optionally includes the acoustic sensor that can include a piezoelectric sensor.

In Example 6, the subject matter of any one or more of Examples 3-5 optionally includes the acoustic sensor that can include a microphone.

In Example 7, the subject matter of any one or more of Examples 1-6 optionally includes the one or more acoustic properties that can include an acoustic signal intensity.

In Example 8, the subject matter of any one or more of Examples 1-7 optionally includes one or more acoustic properties that can include an acoustic signal shape characteristic.

In Example 9, the subject matter of any one or more of Examples 1-8 optionally includes one or more acoustic properties that can include a frequency or spectral content of the received acoustic signal.

In Example 10, the subject matter of any one or more of Examples 1-9 optionally includes the acoustic feedback controller circuit that can be configured to identify the target as one of a plurality of structure types using the measured one or more acoustic properties or one or more spectroscopic properties.

In Example 11, the subject matter of Example 10 optionally includes the acoustic feedback controller circuit that can be configured to identify the target as one of a calculus structure or an anatomical structure using the measured one or more acoustic properties or one or more spectroscopic properties.

In Example 12, the subject matter of Example 11 optionally includes the acoustic feedback controller circuit that can be configured to: classify the target as one of a plurality of calculi types with respective distinct compositions using the measured one or more acoustic properties or one or more spectroscopic properties; and generate the first control signal to the laser system to adjust a laser irradiation parameter setting based on the classification of the target, and to deliver laser energy to the target of the classified calculus type in accordance with the adjusted laser irradiation parameter setting.

In Example 13, the subject matter of any one or more of Examples 11-12 optionally includes the acoustic feedback controller circuit that can be configured to: classify the target as one of a plurality of tissue types using the measured one or more acoustic properties or one or more spectroscopic properties; and generate the first control signal to the laser system to deliver, or withhold delivery of, laser energy in accordance with the classified tissue type.

In Example 14, the subject matter of Example 13 optionally includes the acoustic feedback controller circuit that can be configured to classify the target as a treatment area or a non-treatment area, and to generate the first control signal to the laser system to deliver laser energy to the treatment area, and to withhold delivery of laser energy to the non-treatment area.

In Example 15, the subject matter of any one or more of Examples 13-14 optionally includes the acoustic feedback controller circuit that can be configured to classify the target as normal tissue or cancerous tissue, and to generate the first control signal to the laser system to deliver laser energy to the target of the classified cancerous tissue, and to withhold delivery of laser energy if the target is classified as normal tissue.

In Example 16, the subject matter of any one or more of Examples 1-15 optionally include an optical pathway having a distal portion configured to be inserted into the subject via a longitudinal passage of an endoscope.

In Example 17, the subject matter of Example 16 optionally includes the optical pathway that can include a laser fiber coupled to the laser system and configured to transmit laser energy to the target.

In Example 18, the subject matter of Example 17 optionally includes the optical pathway that can be configured to transmit the acoustic signal to the acoustic feedback controller circuit.

In Example 19, the subject matter of any one or more of Examples 16-18 optionally includes an actuator configured to actuate a longitudinal translation of the optical pathway with respect to the longitudinal passage of an endoscope according to a second control signal generated by the acoustic feedback controller circuit based on the one or more acoustic properties or one or more spectroscopic properties, the longitudinal translation causing a change in position of a distal end of the optical pathway relative to the target.

In Example 20, the subject matter of Example 19 optionally includes the acoustic feedback controller circuit that can be configured to: calculate a distance between the distal end of the optical pathway and the target using the received acoustic signal; and generate the second control signal for actuating longitudinal translation of the optical pathway based on the calculated distance between the distal end of the optical pathway and the target.

In Example 21, the subject matter of any one or more of Examples 19-20 optionally includes the acoustic feedback controller circuit that can be configured to: measure a laser spot size on the target from an image of the target in response to the delivery of laser energy to the target; and generate the second control signal for actuating longitudinal translation of the optical pathway to achieve a desired laser spot size on the target.

Example 22 is a method for controlling a laser system to deliver laser energy to a target in a body of a subject. The method comprises steps of: directing laser energy produced by the laser system at the target via an optical pathway; receiving, via an acoustic sensor, an acoustic signal in response to delivering the laser to the target; measuring, via an acoustic feedback controller circuit, one or more acoustic properties from the received acoustic signal; and generating, via the acoustic feedback controller circuit, a first control signal for controlling the laser system to produce laser energy for delivery to the target based on the one or more acoustic properties.

In Example 23, the subject matter of Example 22 optionally includes generating the first control signal to adjust a laser irradiation parameter setting based on the one or more acoustic properties, and producing laser energy in accordance with the adjusted laser irradiation parameter setting.

In Example 24, the subject matter of any one or more of Examples 22-23 optionally include the one or more acoustic properties that can include one or more of an acoustic signal intensity, an acoustic signal shape characteristic, or a frequency or spectral content of the received acoustic signal.

In Example 25, the subject matter of any one or more of Examples 22-24 optionally includes identifying the target as one of a plurality of structure types using the measured one or more acoustic properties or one or more spectroscopic properties, the plurality of structure types including one of a calculus structure or an anatomical structure.

In Example 26, the subject matter of Example 25 optionally includes: classifying the target as one of a plurality of calculi types with respective distinct compositions using the measured one or more acoustic properties or one or more spectroscopic properties; adjusting a laser irradiation parameter setting for the laser system based on the classification of the target; and generating the first control signal to the laser system to deliver laser energy to the target in accordance with the adjusted laser parameter setting.

In Example 27, the subject matter of any one or more of Examples 25-26 optionally include: classifying the target as one of a plurality of tissue types using the measured one or more acoustic properties or one or more spectroscopic properties; and generating the first control signal to the laser system to deliver, or withhold delivery of, laser energy in accordance with the classified tissue type.

In Example 28, the subject matter of any one or more of Examples 22-27 optionally include adjusting, via an actuator, a position of a distal end of the optical pathway relative to the target based on one or more acoustic properties or one or more spectroscopic properties.

In Example 29, the subject matter of Example 28 optionally includes adjusting the distal end position that can include generating, via the acoustic feedback controller circuit, a second control signal to the actuator to actuate a longitudinal translation of the optical pathway with respect to a longitudinal passage of an endoscope.

In Example 30, the subject matter of any one or more of Examples 28-29 optionally include: measuring a laser spot size on the target from an image of the target in response to the delivery of laser energy to the target; and adjusting, via the actuator, the position of the distal end of the optical pathway to achieve a desired laser spot size on the target.

Example 31 is at least one non-transitory machine-readable storage medium that includes instructions that, when executed by one or more processors of a machine, cause the machine to perform operations comprising: directing laser energy, produced by a laser system, at a target via an optical pathway; receiving, via an acoustic sensor, an acoustic signal in response to delivering the laser to the target; measuring, via an acoustic feedback controller circuit, one or more acoustic properties from the received acoustic signal; and generating, via the acoustic feedback controller circuit, a first control signal for controlling the laser system to produce laser energy for delivery to the target based on the one or more acoustic properties.

In Example 32, the subject matter of Example 31 optionally includes the instructions that cause the machine to perform operations further comprising generating the first control signal to adjust a laser irradiation parameter setting based on the one or more acoustic properties, and producing laser energy in accordance with the adjusted laser irradiation parameter setting.

In Example 33, the subject matter of any one or more of Examples 31-32 optionally include the instructions that cause the machine to perform operation of measuring one or more acoustic properties including one or more of an acoustic signal intensity, an acoustic signal shape characteristic, or a frequency or spectral content of the received acoustic signal.

In Example 34, the subject matter of any one or more of Examples 31-33 optionally include the instructions that cause the machine to perform operations of identifying the target as one of a plurality of structure types using the measured one or more acoustic properties or one or more spectroscopic properties, the plurality of structure types including one of a calculus structure or an anatomical structure.

In Example 35, the subject matter of Example 34 optionally includes the instructions that cause the machine to perform operations of classifying the target as one of a plurality of calculi types with respective distinct compositions using the measured one or more acoustic properties or one or more spectroscopic properties; adjusting a laser irradiation parameter setting for the laser system based on the classification of the target; and generating the first control signal to the laser system to deliver laser energy to the target in accordance with the adjusted laser parameter setting.

In Example 36, the subject matter of any one or more of Examples 34-35 optionally includes the instructions that cause the machine to perform operations including: classifying the target as one of a plurality of tissue types using the measured one or more acoustic properties or one or more spectroscopic properties; and generating the first control signal to the laser system to deliver, or withhold delivery of, laser energy in accordance with the classified tissue type.

In Example 37, the subject matter of any one or more of Examples 31-36 optionally includes the instructions that cause the machine to perform operations of adjusting, via an actuator, a position of a distal end of the optical pathway relative to the target based on one or more acoustic properties or one or more spectroscopic properties.

In Example 38, the subject matter of Example 37 optionally includes the operation of adjusting the distal end position including generating, via the acoustic feedback controller circuit, a second control signal to the actuator to actuate a longitudinal translation of the optical pathway with respect to a longitudinal passage of an endoscope.

In Example 39, the subject matter of any one or more of Examples 37-38 optionally includes the instructions that cause the machine to perform operations including: measuring a laser spot size on the target from an image of the target in response to the delivery of laser energy to the target; and adjusting, via the actuator, the position of the distal end of the optical pathway to achieve a desired laser spot size on the target.

This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 3A-3B illustrate an example of an acoustic signal produced in response to delivery of laser energy and acoustic properties extracted from the acoustic signal.

DETAILED DESCRIPTION

Figure 1:
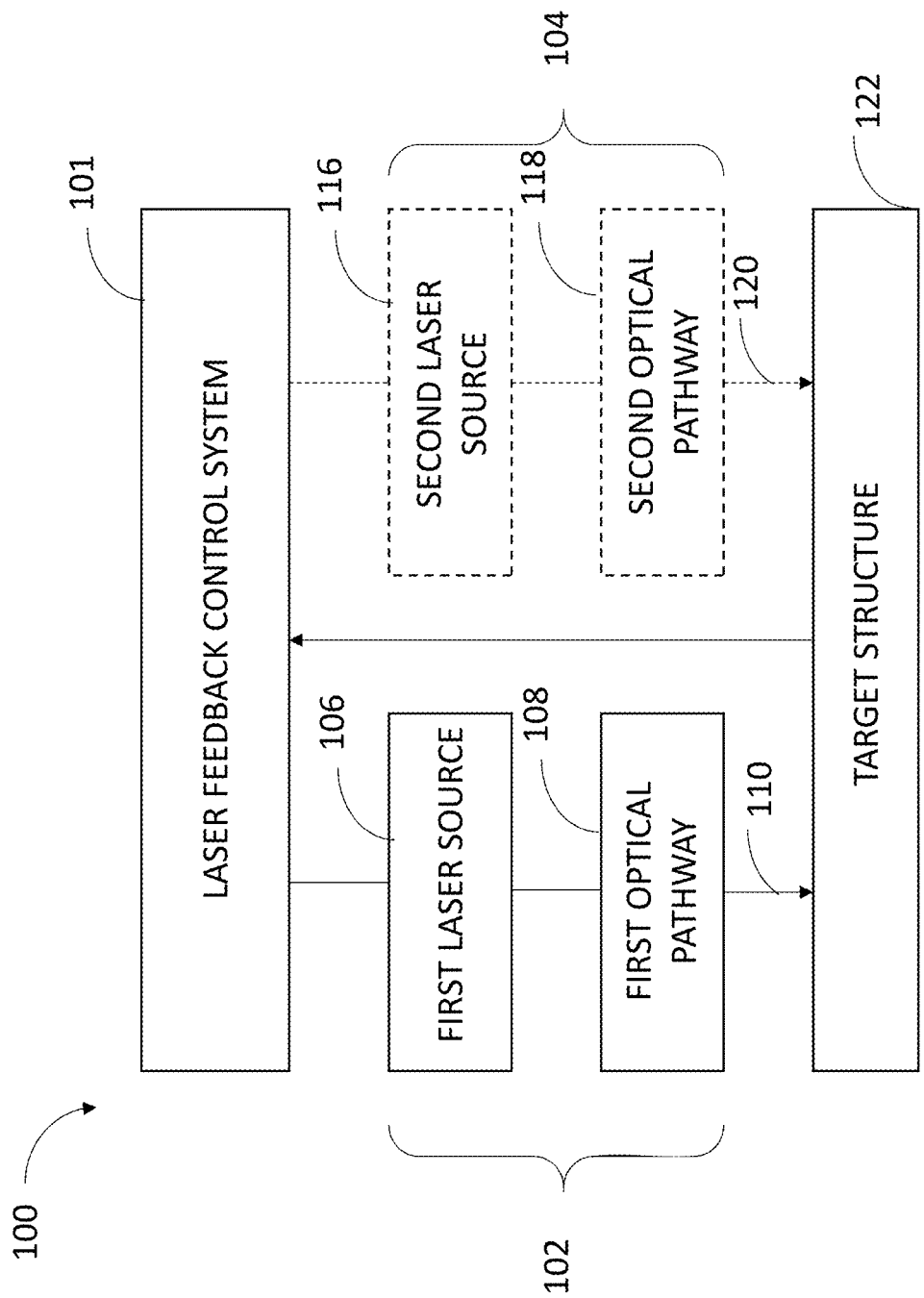
FIG. 1 is a block diagram illustrating an example of a laser energy delivery system configured to provide laser treatment to a target structure in a body, such as an anatomical structure or a calculi structure.

Laser endoscopy is a medical procedure of viewing and operating on an internal organ, and delivering surgical laser to a target body region to achieve a particular diagnostic or therapeutic effect. Laser endoscopy have been used for treatment of soft and hard tissue (e.g., damaging or destroying cancer cells), or in lithotripsy applications. For example, in PCNL, a practitioner can insert a rigid scope through an incision in a patient's back and into the patient's kidney. Through the scope, the practitioner can locate certain stones in the kidney or upper ureter, break the stones into smaller fragments by illuminating the stone, through the scope, with relatively high-powered infrared laser beam. The laser beam can ablate a stone into smaller fragments. The stone fragments can then be withdrawn from the kidney. The scope can include an endoscope, a nephroscope, and/or a cystoscope.

In endoscopic laser treatment, it is desirable to detect the target in real time, recognize target as a particular tissue or calculi type, and apply laser energy only to a treatment structure (e.g., cancerous tissue, or a particular calculi type), and avoid or reduce laser irradiation to non-treatment tissue (e.g., normal tissue). Conventionally, the recognition of a target treatment structure of interest is performed manually by an operator, such as by visualizing the target surgical site and its surrounding environment through an endoscope. Such a manual approach may be less accurate in certain circumstances where a tight access to an operation site offers a limited surgical view. Biopsy techniques have been used to extract the target structure out of the body to analyze its composition in vitro. However, in many clinical applications, it is desirable to determine tissue composition in vivo to reduce surgery time and improve therapy efficacy. For example, in laser lithotripsy, automatic recognition of calculi type in vivo and distinguishing it from surrounding tissue would allow a physician to adjust an irradiation parameter setting (e.g., laser power or exposure time) to more effectively ablate the target stone, while at the same time avoid irradiating non-treatment tissue neighboring the target stone.

Conventional endoscopic laser treatment also has a limitation that tissue type (e.g., composition) cannot be continuously monitored in a procedure. There are many moving parts during an endoscopic procedure, and the tissue viewed at from the endoscope may change throughout the procedure. Because the conventional biopsy techniques require the removal of a tissue sample to identify its type, they cannot be used to monitor tissue type throughout the procedure. Continuous monitoring and recognition of structure type (e.g., soft or hard tissue type, normal tissue versus cancerous tissue, or composition of calculi structures) at the tip of the endoscope may give physicians more information to better adapt the treatment during the procedure. For example, if a physician is dusting a renal calculi that has a hard surface, but a soft core, continuous tissue composition information through the endoscope may allow the physician to adjust the irradiation parameter setting based on the continuously detected stone surface composition, such as from a first setting that perform better on the hard surface of the stone to a second different setting that perform better on the soft core of the stone.

For at least the above reasons, the present inventors have recognized an unmet need for systems and methods that are capable of identifying different structure types with respective distinct compositions in vivo, and adjusting therapy according to the identification of structure types.

Described herein are systems, devices, and methods for automatic control of laser treatment of target structure in a body of a subject based on acoustic feedback in response to delivery of laser energy to the target. An exemplary endoscopic laser energy delivery system comprises a laser system to direct laser energy at a target in a body of a subject, and an acoustic feedback controller circuit to receive an acoustic signal in response to delivery of laser energy to the target, to measure one or more acoustic properties from the received acoustic signal, and to generate a first control signal for controlling the laser system to produce laser energy for delivery to the target, such as by adjusting a laser irradiation parameter setting based on the one or more acoustic properties. The control circuit may generate a second control signal to an actuator to adjust a position of a laser fiber distal end relative to the target to achieve a desired therapeutic effect.

The systems, devices, and methods according to various embodiments discussed herein improve real-time and in vivo target identification during a laser endoscopy procedure. Features described herein may further be used in regard to an endoscope, laser surgery, laser lithotripsy, irradiation parameter settings, and/or spectroscopy. Examples of targets and applications may include laser lithotripsy of renal calculi and laser incision or vaporization of soft tissue. In an example of endoscopic system that incorporate the features as described herein, tissue or calculi types may be identified and monitored in vivo, and used for adjusting laser energy and delivery, such as an irradiation parameter setting (e.g., one or more laser pulse parameters such as intensity, power, duration, frequency, or pulse shape, exposure time, or firing angle), for optimal laser treatment. The capability of continuous monitoring and identification of tissue types or calculi types allow for the instant adjustment of laser treatment. With improved recognition and classification of target structure, the patient may be protected from accidental laser firing or misplaced laser firing, and improved therapy efficacy and tissue safety may be achieved.

According to some examples discussed in this document, acoustic feedback during laser firing at the target may be used for identifying tissue or calculi types or composition, adjusting irradiation parameter settings, and/or adjusting delivery of the laser energy such as by controllably adjusting a laser fiber position or orientation relative to a target, such as to achieve a desired distance between a distal end of the laser fiber and the target (also referred to as fiber-target distance). The acoustic feedback may include acoustic signals produced when a laser pulse propagates through the media (e.g., liquid and vapor) along the path to the target and causes the liquid and vapor to vibrate, and when the laser pulse projects to the target and causes the target to vibrate. In accordance to various examples discussed herein, the fiber-target distance may be estimated using acoustic feedback signal. An actuator may controllably adjust the position or orientation of a distal portion of the laser fiber relative to a target. In some examples, the laser may be locked (i.e., prevented from firing) if an appropriate targeted element (e.g., cancerous lesion or calculi) is not within a laser firing range. For example, during a laser lithotripsy procedure, the laser may be locked if no stone is within the laser firing range (e.g., only tissue is within laser range). The automatic locking control or fiber-target distance adjustment may ensure a target is within optimum firing distance to improve performance of an existing laser lithotripsy system, conserve power, enhance patient safety, and improves efficacy of stone ablation.

The acoustic-feedback laser energy delivery system discussed herein may be advantageous over conventional laser energy delivery system utilizing other types of feedback. For example, visual feedback may be constrained by human reaction time, which can be long relative to fast laser-target interaction and processes (e.g., formation of bubbles at the fiber tip, time nonlinear laser light absorption in water/vapor media and by stone material, vibrations, and other instabilities). Additionally, human reaction time may be significantly variable among human operators. In contrast, the acoustic waves have a fast propagation speed through tissue, calculi, and surrounding liquid media, such that the latency from sound formation to acquiring the feedback and adjusting the laser energy or laser delivery accordingly may be reduced.

A high-speed acoustic feedback system as discussed in this document allows for faster, real-time laser treatment control including, for example, irradiation parameter setting and/or laser fiber position or orientation, with enhanced precision. Generally, there is a tradeoff between fiber flexibility and ablation speed for optical fibers that range in diameter from 150 µm to 1000 µm. Larger diameter fibers generally provide a higher ablation speed, and smaller diameter fibers tend to be more flexible. Faster adjustment of fiber position may help achieve a desired laser spot size on the target, thereby improving laser ablation speed with a small diameter fiber. As such, the high-speed acoustic feedback system discussed herein allows an operator to use more flexible optical fibers with small diameter (e.g., ~150 µm-365 µm) to achieve a high ablation speed similar to using large diameter fibers (e.g., ~500 µm-1000 µm). The high-speed acoustic feedback system may also facilitate creation of consistent bubble tunnel in the media between laser fiber and target to significantly reduce laser light losses due to water absorption.

Another advantage of the acoustic-feedback laser energy delivery system discussed herein is that laser treatment may be optimized without detailed knowledge about type of the target and the media condition between laser fiber and the target. Such a therapy optimization approach may stabilize or maximize preselected therapy goal with improved efficiency. For example, the laser ablation speed depends on applied laser power density, and the intensity of the acoustic signal (e.g., acoustic signal peak amplitude) produced in response to laser firing at a target is correlated to laser power density. The laser energy delivery system discussed here may automatically adjust fiber position and laser power to maximize an acoustic signal peak amplitude. Compared to other in vivo feedback-controlled laser treatment, the acoustic feedback system as described herein can advantageously enable more precise and faster therapy control, reduce procedure time, and improve laser treatment efficiency.

FIG. 1 is a block diagram illustrating an example of a laser energy delivery system 100 configured to provide laser treatment to a target structure 122 in a body of a subject, such as anatomical structure (e.g., soft tissue, hard tissue, or abnormal such as cancerous tissue) or calculi structure (e.g., kidney or pancreobiliary or gallbladder stone). In an example, the system 100 is an endoscopic laser energy delivery system. The laser energy delivery system 100 includes a laser feedback control system 101 and at least one laser system 102. The laser feedback control system 101 may receive feedback signals 130 from the target. Various feedback signals may be used to control laser delivery. In an example, the feedback signals 130 may include an acoustic signal. The acoustic signal may be sensed when a laser pulse propagates through the media (e.g., liquid and vapor) along the path to the target and causes the liquid and vapor to vibrate, and when the laser pulse projects to the target and causes the target to vibrate. In another example, the feedback signals 130 may include reflected electromagnetic signal (e.g., reflected illumination light emitted from a light source). In yet another example, the feedback signals 130 may include reflected laser signal. The laser feedback control system 101 may analyze the feedback signals 130, generate one or more signal properties such as acoustic properties from the acoustic signal or spectroscopic properties from the reflected electromagnetic signal, and control laser energy output and/or laser delivery. The laser feedback control system 101 may be used in various applications, such as industrial and/or medical applications for treatment of soft (e.g., non-calcified) or hard (e.g., calcified) tissue, or calculi structures such as kidney or pancreobiliary or gallbladder stones. In some examples, the laser energy delivery system 100 may deliver precisely controlled therapeutic treatment of tissue or other anatomical structures (e.g., tissue ablation, coagulation, vaporization, or the like) or treatment of non-anatomical structures (e.g., ablation or dusting of calculi structures).

The laser feedback control system 101 may be in operative communication with one or more laser systems. FIG. 1 shows the laser feedback system connected to a first laser system 102 and optionally (shown in dotted lines) to a second laser system 104. Additional laser systems are contemplated within the scope of the present disclosure. The first laser system 102 may include a first laser source 106, and associated components such as power supply, display, cooling systems and the like. The first laser system 102 may also include a first optical pathway 108 operatively coupled with the first laser source 106. In an example, the first optical pathway 108 includes an optical fiber. The first optical pathway 108 may be configured to transmit laser beams from the first laser source 106 to the target structure 122.

Based on the analysis of the feedback signals 130, the laser feedback control system 101 may control the first laser system 102 and/or the second laser system 104 to generate suitable laser outputs for providing a desired therapeutic effect. For instance, the laser feedback control system 101 may monitor properties of the target structure 122 during a therapeutic procedure (e.g., ablating calculi such as kidney stones into smaller fragments) to determine if the tissue was suitably ablated prior to another therapeutic procedure (e.g., coagulation of blood vessels).

In an example, the first laser source 106 may be configured to provide a first output 110. The first output 110 may extend over a first wavelength range, such as one that corresponds to a portion of the absorption spectrum of the target structure 122. The first output 110 may provide effective ablation and/or carbonation of the target structure 122 since the first output 110 is over a wavelength range that corresponds to the absorption spectrum of the tissue.

In an example, the first laser source 106 may be configured such that the first output 110 emitted at the first wavelength range corresponds to high absorption (e.g., exceeding about 250 cm$^{-1}$) of the incident first output 110 by the tissue. In example aspects, the first laser source 106 may emit first output 110 between about 1900 nanometers (nm) and about 3000 nm (e.g., corresponding to high absorption by water) and/or between about 400 nm and about 520 nm (e.g., corresponding to high absorption by oxy-hemoglobin and/or deoxy-hemoglobin). Appreciably, there are two main mechanisms of light interaction with a tissue: absorption and scattering. When the absorption of a tissue is high (absorption coefficient exceeding 250 cm$^{-1}$) the first absorption mechanism dominates, and when the absorption is low (absorption coefficient less than 250 cm$^{-1}$), for example lasers at 800-1100 nm wavelength range, the scattering mechanism dominates.

Various commercially available medical-grade laser systems may be suitable for the first laser source 106. For instance, semiconductor lasers such as InXGa1-XN semiconductor lasers providing the first output 110 in the first wavelength range of about 515 nm and about 520 nm or between about 370 nm and about 493 nm may be used. Alternatively, infrared (IR) lasers such as those summarized in Table 1 below may be used.

TABLE 1

Example List of suitable IR lasers

| Laser | Wavelength $\lambda$ (nm) | Absorption Coefficient $\mu_s$ (cm$^{-1}$) | Optical Penetration Depth $\delta$ (μm) |
| --- | --- | --- | --- |
| Thulium fiber laser: | 1908 | 88/150 | 114/67 |
| Thulium fiber laser: | 1940 | 120/135 | 83/75 |
| Thulium:YAG: | 2010 | 62/60 | 161/167 |
| Holmium:YAG: | 2120 | 24/24 | 417/417 |
| Erbium:YAG: | 2940 | 12,000/1,000 | 1/10 |

The optional second laser system 104 may include a second laser source 116 for providing a second output 120, and associated components, such as power supply, display, cooling systems and the like. The second laser system 104 may either be operatively separated from or, in the alternative, operatively coupled to the first laser source 106. In some embodiments, the second laser system 104 may include a second optical pathway 118 (separate from the first optical pathway 108) operatively coupled to the second laser source 116 for transmitting the second output 120. Alternatively, the first optical pathway 108 may be configured to transmit both the first output 110 and the second output 120.

In certain aspects, the second output 120 may extend over a second wavelength range, distinct from the first wavelength range. Accordingly, there may not be any overlap between the first wavelength range and the second wavelength range. Alternatively, the first wavelength range and the second wavelength range may have at least a partial overlap with each other. In advantageous aspects of the present disclosure, the second wavelength range may not correspond to portions of the absorption spectrum of the target structure 122 where incident radiation is strongly absorbed by tissue that has not been previously ablated or carbonized. In some such aspects, the second output 120 may advantageously not ablate uncarbonized tissue. In another embodiment, the second output 120 may ablate carbonized tissue that has been previously ablated. In additional embodiments, the second output 120 may provide additional therapeutic effects. For instance, the second output 120 may be more suitable for coagulating tissue or blood vessels.

Figure 2:
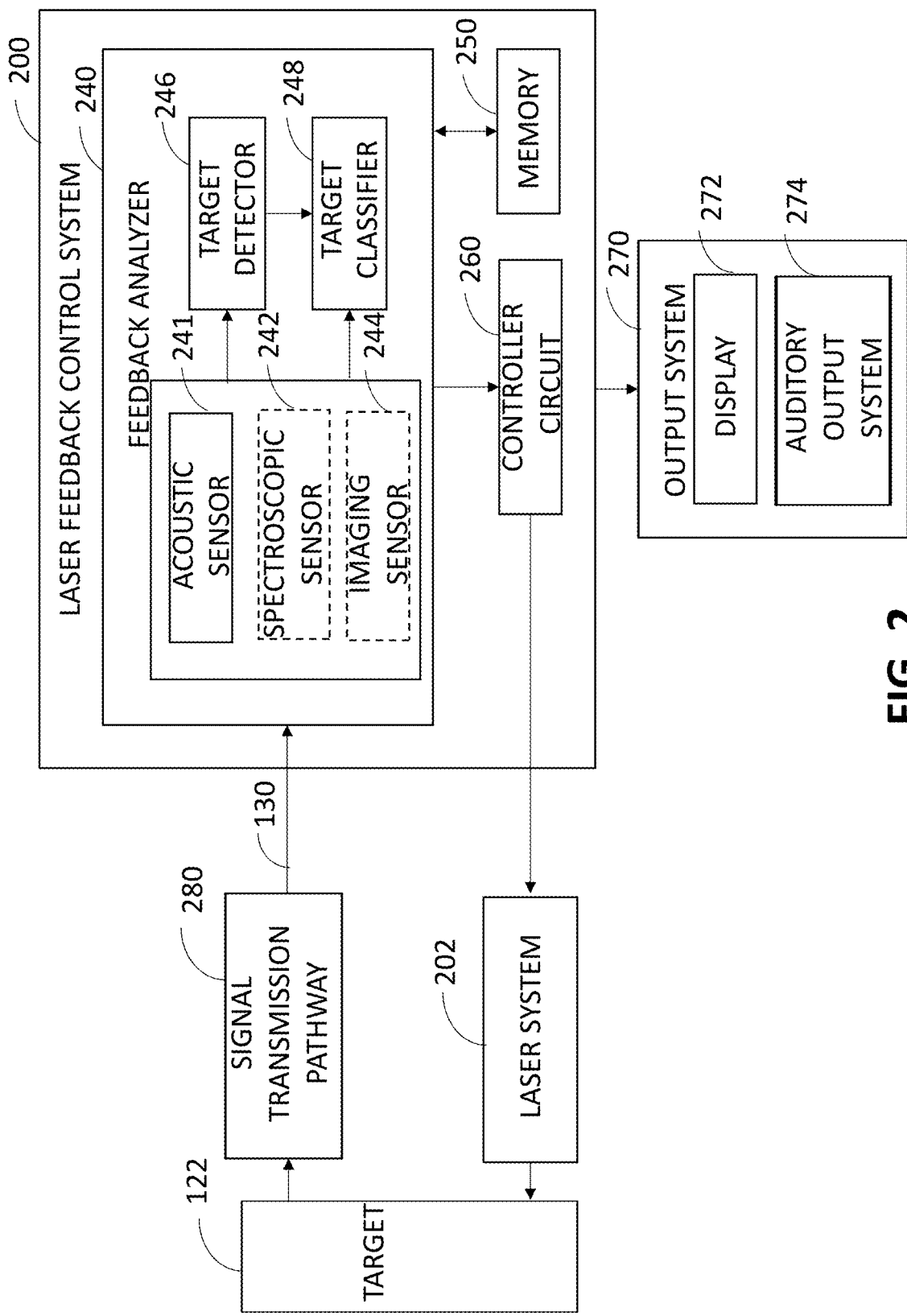
FIG. 2 is a block diagram illustrating a laser feedback control system and a part of the environment in which said system may be used.

FIG. 2 is a block diagram illustrating a laser feedback control system 200 and at least a part of the environment in which it may be used. The laser feedback control system 200, which is an example of the laser feedback control system 101, includes a feedback analyzer 240, a memory 250, and a controller circuit 260. The feedback analyzer 240 may, according to one aspect of the subject matter described herein, include an acoustic sensor 241 configured to sense an acoustic signal in response to delivery of laser energy to the target. The acoustic signal may be sensed when a laser pulse propagates through the media (e.g., liquid and vapor) along the path to the target and causes the liquid and vapor to vibrate, and when the laser pulse projects to the target and causes the target to vibrate. In some examples, the acoustic sensor 241 may sense certain sound waves with specific wavelengths, such as audible range of waves, ultrasonic wave, or infrasonic waves. Examples of the acoustic sensor 241 may include microphones, hydrophones, capacitive sensors, piezoelectric sensor, piezoceramic sensor, fiber-optic sensors, or solid-state acoustic detectors, among others. The feedback analyzer 240 may analyze the acoustic signals to generate one or more acoustic properties. Examples of the acoustic properties may include intensity, power, frequency or spectral content, or a graphical feature representing a shape of the received acoustic signal (e.g., a shape characteristic of a time series of sound intensity). In some examples, the acoustic properties may include one or more statistical features (e.g., signal mean or variance) of the received acoustic signal.

The feedback analyzer 240 may optionally include a spectroscopic sensor 242 that may sense a spectroscopic signal reflected from the target structure 122, and generate one or more spectroscopic properties from the reflected signal. The spectroscopic properties may include characteristics such as reflectivity, reflectance spectrum, absorption index, and the like. Examples of the spectroscopic sensor 242 may include a Fourier Transform Infrared (FTIR) spectrometer, a Raman spectrometer, a UV-VIS spectrometer, a UV-VIS-IR spectrometer, or a fluorescent spectrometer, among others. Each spectroscopic sensor 242 corresponds to a spectroscopy technique. For example, UV-VIS reflection spectroscopy may be used to gather information from the light reflected off an object similar to the information yielded from the eye or a color image made by a high resolution camera, but more quantitatively and objectively. The reflection spectroscopy may offer information about the material since light reflection and absorption depends on its chemical composition and surface properties. Information about both surface and bulk properties of the sample may be obtained using this technique. The reflection spectroscopy may be used to recognize composition of hard or soft tissue. Fluorescent spectroscopy is a type of electromagnetic spectroscopy that analyzes fluorescence from a sample. It involves using a beam of light, usually ultraviolet, that excites a material compound and causes the material compound to emit light, typically in visible or IR area. The method may be applied for analysis of some organic components such as hard and soft tissue. FTIR spectroscopy may be used for rapid materials analysis, and has relatively good spatial resolution and gives information about the chemical composition of the material. Raman spectroscopy may be used for identifying hard and soft tissue components. As a high spatial resolution technique, it is also useful for determining distribution of components within a target. The spectroscopy techniques as described above may be used alone or in combination to analyze the spectroscopic signal by the spectroscopic sensor 242 to generate one or more spectroscopic properties indicative of structure types with respective distinct compositions.

The feedback analyzer 240 may optionally include an imaging sensor 244 such as an imaging camera, such as a CCD or CMOS camera sensitive in ultraviolet (UV), visible (VIS) or infrared (IR) wavelengths in an embodiment. In some embodiments, the spectroscopic sensor 242 may include more than a single type of spectrometer or imaging camera listed herein to enhance sensing and detection of various features (e.g., carbonized and non-carbonized tissue, vasculature, and the like).

The acoustic sensor 241, and optionally the spectroscopic sensor 242 and/or the imaging sensor 244, may be operatively coupled to a signal transmission pathway 280. The signal transmission pathway 280 may include an optical pathway (e.g., an optical fiber) with optical properties suitable for transmitting the feedback signals 130 (e.g., acoustic signals or spectroscopic signals reflected from the tissue). Alternatively, the acoustic sensor 241, and optionally the spectroscopic sensor 242 and/or the imaging sensor 244, may be operatively coupled to the first optical pathway 108 and/or the second optical pathway 118 of the second laser system 104 to detect respective feedback signals via the first optical pathway 108 and/or the second optical pathway 118.

The feedback analyzer 240 may include a target identifier that may detect and identify a target. In an example as illustrated in FIG. 2, the target identifier may include one or more of a target detector 246 or a target classifier 248. For a tissue target or a calculi target, its ability to absorb laser energy depends on its composition and liquid content. Different target types, such as different calculi structures or soft or hard tissue, may have different composition and/or liquid content. When these targets absorb different amount of laser energy, they may produce respective different vibration patterns that may be sensed as different acoustic properties. The target detector 246 may use one or more acoustic signal properties to identify the target structure 122 as one of a plurality of structure categories, such as a category of calculi structure, or a category of anatomical structure. Examples of calculi structure may include stones or stone fragments in various stone-forming regions such as urinary system, gallbladder, nasal passages, gastrointestinal tract, stomach, or tonsils. Examples of the anatomical structure may include soft tissue (e.g., muscles, tendons, ligaments, blood vessels, fascia, skin, fat, and fibrous tissues), hard tissue such as bone, connective tissue such as cartilage, among others.

The target classifier 248 may classify the target structure 122 as one of a plurality of structure types of the same category, such as a particular tissue type within an identified category of anatomical structure, or as a particular calculi type within an identified category of calculi structure. In an example, the target classifier 248 may classify an identified calculus as one of stone types with distinct chemical compositions, such as one of a CaP stone, a MAP stone, a COM stone, a COD stone, a cholesterol-based stone, or a uric acid (UA) stone. The classification may be made based on one or more acoustic properties, such as intensity, power, frequency or spectral content, or a graphical feature or shape of the received acoustic signal, or one or more statistical features generated from the received acoustic signal. In some example, the target classifier 248 may classify an identified anatomical structure as one of plurality of tissue types. The tissue types may include tissue at distinct anatomical locations, such as calyx tissue, cortex tissue, medulla tissue, or ureter tissue. In another example, the target classifier 248 may be configured to classify an identified anatomical structure as normal tissue or abnormal tissue (e.g., cancerous tissue). In another example, the classifier 248 may be configured to classify an identified anatomical structure as a treatment area (e.g., tumor or polyp intended for removal) or a non-treatment area (e.g., blood vessels, muscle, etc.). The classification may be made based on one or more acoustic properties, such as intensity, power, frequency or spectral content, or a graphical feature or shape of the received acoustic signal, or one or more statistical features generated from the received acoustic signal, as described above. Examples of the acoustic signal produced in response to delivery of laser energy and various acoustic properties are discussed below, such as with reference to FIGS. 3A-3B.

In some examples, the target detector 246 or the target classifier 248 may use additional feedback to identify the target structure 122 as a calculi structure or anatomical structure, or to classify the target structure 122 as a specific calculi type or tissue type. Examples of such additional feedback may include, for example, one or more spectroscopic signal properties generated from the spectroscopic signal, or one or more imaging properties generated from the imaging signal.

The controller circuit 260 may be in operative communication with the feedback analyzer 240 and a laser system 202. The laser system 202 may represent the first laser system 102, the optional second laser system 104, and/or any additional laser systems. The controller circuit 260 may control the laser system 202 operatively connected thereto according to one or more control algorithms described herein to control the laser outputs from the one or more laser systems to produce a desired therapeutic effect in the target structure 122. In an example, the controller circuit 260 may generate a first control signal to the laser system 202 to adjust a laser irradiation parameter setting based on at least the acoustic feedback, such as one or more acoustic properties. Examples of the laser irradiation parameters may include wavelength, power, power density, pulse parameters (e.g., pulse width, pulse rate, amplitude, duty cycle), exposure time, total dose or energy, among others. In an example, the controller circuit 260 may generate a second control signal to an actuator to automatically adjust a position or orientation of a distal portion of an optical fiber for delivering laser pulses, such as to change a distance between the fiber distal end and the target structure 122 (the "fiber-target distance") based on at least the received acoustic signal. In an example, the feedback analyzer 240 may calculate or estimate the fiber-target distance using one or more acoustic properties derived from the acoustic signal, and the controller circuit 260 may adjust the laser fiber position or orientation such that the target is within a desired laser firing distance.

According to example embodiments, the controller circuit 260 may include processors, such as microprocessors, digital signal processors (DSPs), application specific integrated circuits (ASICs), field programmable gate arrays (FPGAs), or any other equivalent integrated or discrete logic circuitry, as well as any combinations of such components for performing one or more of the functions attributed to the controller circuit 260. Optionally, the controller circuit 260 may be coupled by wired or wireless connections to the feedback analyzer 240 and the laser system 202. The controller circuit 260 may communicate with the feedback analyzer 240 (e.g., over wired or wireless connections), and determine an operating mode of the laser system 202 based on the identification of the target structure 122 (such as determined by the target detector 246), or based on the classification of the target structure 122 (such as determined by the target classifier 248).

In some examples, the laser system 202 may be associated with one of two distinct operating modes or states: a first state wherein the laser system 202 generates a laser output, and a second state where a laser system 202 does not generate a laser output. For instance, the first laser system 102 may have a first state where a first output 110 (e.g., over the first wavelength range) is generated, and a second state where the first output 110 is not generated. Similarly, the second laser system 104 may have a first state where a second output 120 (e.g., over the second wavelength range) is generated, and a second state where the second output 120 is not generated. In such embodiments, the controller circuit 260 may control the laser system 220 by sending control signals that change the operating state the laser system from the first state to the second state, or from the second state to the first state. In some examples, the laser system 202 may have additional states, for instance, a third state where a laser output in accordance with a different laser irradiation parameter setting is generated. Accordingly, additional control signals may be sent by the controller circuit 260 to the laser system(s) to change their states from their current state to one or more additional states (e.g., first state to third state, second state to third state, third state to first state, and third state to second state) to generate laser outputs that provide a desired therapeutic effect.

In an example, the controller circuit 260 may generate a control signal to operate the laser system 202 in a first operating mode if the target is identified as a calculi structure, or a second operating mode if the target is identified as an anatomical structure, or a third operating mode if the target is identified as neither an anatomical structure nor a calculi structure. In an example, the first operating mode may include activating the laser system 202 to deliver a laser beam programmed with a first irradiation parameter setting to ablate or dust the identified calculi, such as kidney stones. In an example, the second operating mode may include withholding laser delivery, or delivering a laser beam programmed with a second irradiation parameter setting different from the first irradiation parameter setting to an identified tissue. In an example, the third operating mode may include deactivating the laser system 202 from delivery of laser energy. The laser irradiation parameters may include wavelength, power, power density, pulse parameters (e.g., pulse width, pulse rate, amplitude, duty cycle), exposure time, total dose or energy, among others.

In some examples, the controller circuit 260 may determine the operating mode of the laser system 202 based on the classification of the target structure 122 as one of a plurality of calculi types, such as CaP stone, a MAP stone, a COM stone, a COD stone, a cholesterol-based stone, or a uric acid (UA) stone, as determined by the target classifier 248. The controller circuit 260 may adjust the irradiation parameter setting based on the classification of calculi type, and generate a control signal to control the laser system 202 to deliver laser energy to the target structure 122 in accordance with the adjusted irradiation parameter setting.

In some examples, the controller circuit 260 may determine the operating mode of the laser system 202 based on the classification of the target structure 122 as one of a plurality of tissue types, such as renal tissue at different anatomical locations (e.g., calyx tissue, cortex tissue, medulla tissue, or ureter tissue), normal or abnormal tissue (e.g., cancerous tissue), treatment area (e.g., tumor or polyp intended for removal) or a non-treatment area (e.g., blood vessels, muscle, etc.). The controller circuit 260 may adjust the irradiation parameter setting based on the classification of tissue type, and generate a control signal to the laser system 202 that delivers laser energy to the identified anatomical structure in accordance with the adjusted irradiation parameter setting.

In some examples, irradiation parameter settings may be determined respectively for a plurality of calculi types and/or for a plurality of tissue types. A calculi type-irradiation parameter setting correspondence, or a tissue type-irradiation parameter setting correspondence, may be created and stored in the memory 250, such as in a lookup table, an associative array, or the like. The controller circuit 260 may use one of such stored correspondence to determine an irradiation parameter setting that corresponds to the classified calculi type or the classified tissue type.

In some examples, the controller circuit 260 may adjust the irradiation parameter setting directly based on one or more acoustic properties produced by the feedback analyzer 240 without using information about target type or target composition such as generated by the target detector 246 or the target classifier 248. For example, the intensity of the acoustic signal produced in response to laser firing at a target calculi structure is correlated to laser power density. The controller circuit 260 may automatically adjust an irradiation parameter setting (e.g., laser power) and laser fiber position to achieve a desired acoustic signal amplitude.

In various examples, the feedback analyzer 240 may continuously monitor the target structure 122, collect and analyze feedback signals, and continuously communicate with the controller circuit 260. Accordingly, the controller circuit 260 may continue maintaining the laser systems in one or more states until a change in the feedback is detected (e.g., a different category of the target structure 122, a different tissue type, or a different calculi type). When a change in feedback is detected, the controller circuit 260 may communicate with the one or more laser systems and change their state(s) to deliver a desired therapeutic effect. Alternatively or additionally, the controller circuit 260 may communicate with an operator (e.g., healthcare professional), and display one or more output(s) via one or more output system(s) indicative of the feedback signal, and may, optionally, instruct the operator to perform one or more treatment procedures with the first laser system and/or the second laser system to deliver a desired therapeutic effect.

In illustrative examples described herein, the controller circuit 260 may control more than one laser system by changing the operating state of each laser system. According to an aspect, the controller circuit 260 may independently control each laser system. For instance, the controller circuit 260 may send a distinct control signal to each laser system to control each laser system independently of the other laser systems. Alternatively, the controller circuit 260 may send a common signal to control one or more laser systems.

The laser feedback control system 200 may be in operative communication with an output systems 270. The output system 270 may communicate with and/or deliver signals received and information produced by the feedback analyzer 240 to users and/or to other systems such as an irrigation suction/pumping system used for a therapeutic treatment, or an optical display controller, or other systems. Examples of the signals and information delivered may include one or more of the feedback signal 130 (e.g., the acoustic signals, and optional spectroscopic signal and imaging signal), signal properties (e.g., the acoustic properties generated, optional spectroscopic properties and imaging properties), identification of the target structure 122 generated by the target detector 246, or classification of the target structure 122 generated by the target classifier 248. In an example, the output system 270 may include a display 272, such as a screen (e.g., a touchscreen), or in the alternative, a visual indicator (e.g., LED lights of one or more colors). In an example, the output system 270 may include an auditory output systems 274 capable of providing auditory signals (e.g., speakers, an alarm system and the like). The output system 270 may provide one or more outputs (e.g., LED lights of a first color, a first message on the screen, an alarm sound of a first tone) to indicate that a desired therapeutic effect (e.g., ablation of calculi structures such as kidney stones, or carbonation of abnormal tissue such as cancerous tissue) has been achieved. In some examples, the output system 270 may provide one or more different outputs when desired therapeutic effects have not been achieved. For instance, output system 270 may provide one or more outputs (e.g., LED lights of a second color, a second message on the screen, an alarm sound of a second tone) to indicate that a desired therapeutic effect has not been achieved. In some examples, therapeutic effects on different identified structure categories (e.g., calculi versus anatomical structures) or different classified structure types may be indicated on the output system 270 using respectively different outputs (e.g., LED lights of different colors, different messages on the screen, or different tones of alarm). Such outputs may prompt the operator (e.g., a health care professional) to take proper actions such as providing additional treatment using the one or more laser systems.

FIGS. 3A-3B illustrate an example of an acoustic signal produced in response to delivery of laser energy and acoustic properties extracted from the acoustic signal. FIG. 3A illustrates an example of a portion of an endoscopic laser lithotripsy system comprising an endoscope 301 and an optical pathway 302 at least partially located within a longitudinal passage of the endoscope 301. In the example as shown in FIG. 3A, the optical pathway 302, which is an example of the first optical pathway 108 or the second optical pathway 118, has a distal end 304 extending from the distal end of the endoscope 301. In an example, the optical pathway 302 may include an optical fiber, or a laser fiber. Laser pulses, such as generated from the first laser source 106 or the second laser source 116, may be transmitted through the optical pathway 302. The distal end 304 of the optical pathway 302 may direct laser pulses at a calculi target 322.

FIG. 3B illustrates an example of an acoustic signal 350, such as sensed by the acoustic sensor 241, in response to a laser pulse 340 that begins at time instant $t_0$ and ends at time instant $t_E$. As the laser pulse propagates through the liquid media 332 and vapor bubbles 334, the liquid and vapor absorb laser energy and vibrate, generating pressure waves that may be sensed by the acoustic sensor as an acoustic signal. As illustrated in FIG. 3B, the acoustic signal 350 has a time-varying signal strength with a first peak 351 at $t_1$ corresponding to maximal liquid vibration, and a second peak 353 at $t_2$ corresponding to maximal vapor vibration. When the laser pulse reaches the target, the calculi target 322 absorbs laser energy and vibrates, generating pressure waves that may be sensed by the acoustic sensor as an acoustic signal peak 355 at $t_3$. The time intervals from $t_0$ to the acoustic signal peaks 351, 353, and 355 (that is, $t_1-t_0$, $t_2-t_0$, and $t_3-t_0$) are correlated to the distances that the laser pulse has traveled along the propagation path from the optical pathway distal end 304. According to various examples as described in this disclosure, such time intervals may be used to control the delivery of laser e The acoustic signals 350 may be processed such as by the feedback analyzer 240 to generate one or more acoustic properties, including, for example, intensity, power, frequency or spectral content, or a graphical feature or shape of the received acoustic signal. In some examples, the acoustic properties may include one or more statistical features of the acoustic signal (e.g., signal mean or variance). The controller circuit 260 may adjust the irradiation parameter setting based on one or more acoustic properties. For example, the intensity of the acoustic signal (e.g., the amplitude of acoustic signal peak 355) produced in response to laser firing at a target calculi structure is correlated to laser power density. The controller circuit 260 may automatically adjust an irradiation parameter setting (e.g., power, power density, pulse parameters, exposure time, total dose or energy), and/or adjust the laser fiber position or orientation, to achieve a desired acoustic signal intensity, such as to maximize the amplitude of acoustic signal peak 355.

In some examples, the controller circuit 260 may adjust the irradiation parameter setting and/or the laser fiber position or orientation based on identification of calculi target 322 as one of a plurality of calculi types with distinct compositions using the one or more acoustic properties generated from the acoustic signal, such as by using the target detector 246 and/or target classifier 248.

In some examples, the controller circuit 260 may calculate or estimate a fiber-target distance using one or more acoustic properties derived from the acoustic signal, such as temporal information about an acoustic signal peak corresponding to laser firing at the target. For example, a time interval between $t_0$ and $t_3$ ($t_3-t_0$) represents laser pulse travel time from the laser fiber distal end 304 to the target 322, which is correlated to the laser-target distance. The controller circuit 260 may estimate the fiber-target distance using the interval $t_3-t_0$. The controller circuit 260 may generate a control signal to an actuator to automatically adjust the laser fiber position relative to the target, such as to obtain or maintain a desired fiber-target distance.

Figure 4:
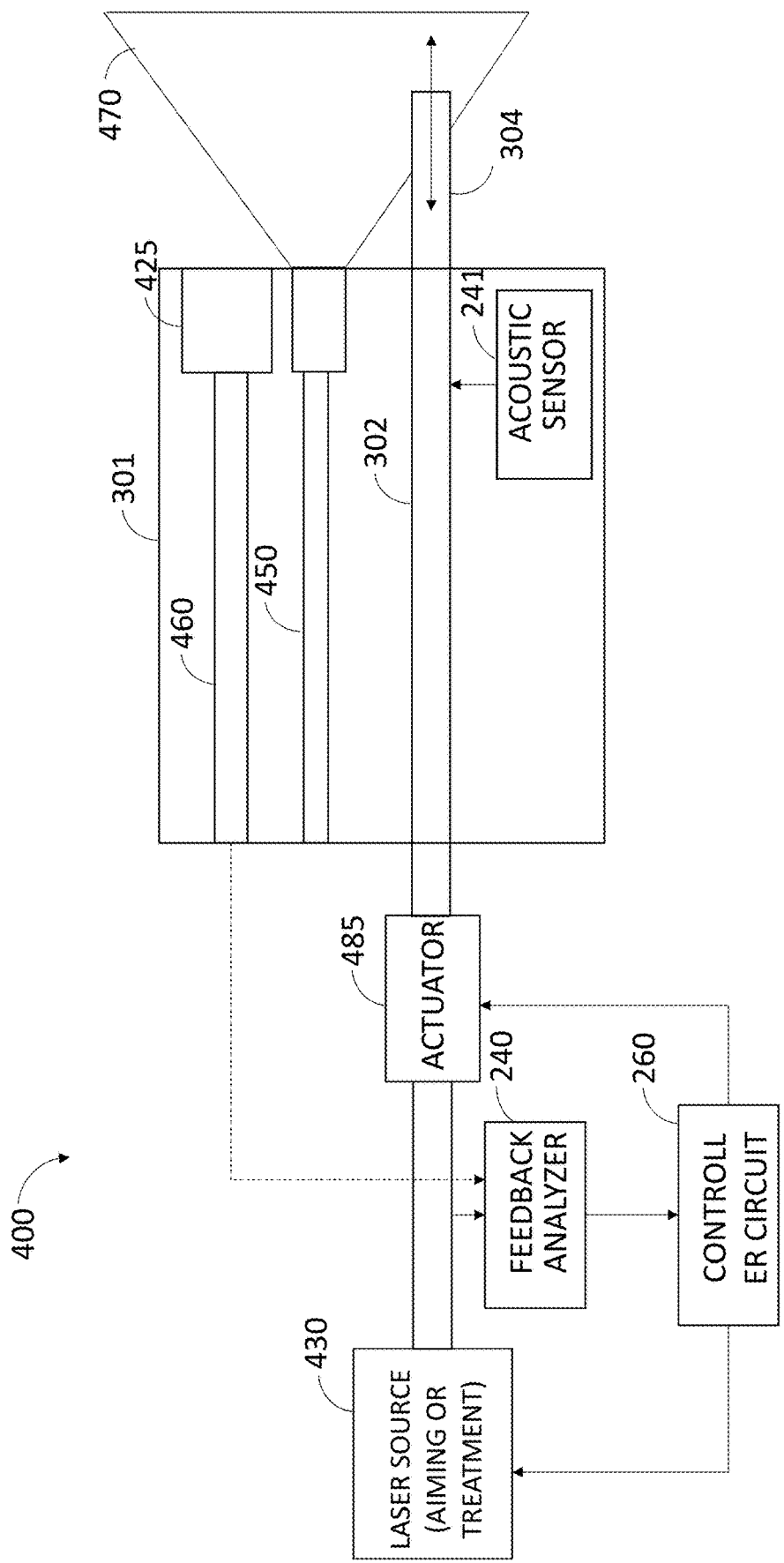
FIG. 4 illustrate an example of an endoscopic laser lithotripsy system that can control and adjust a position of an optical pathway with respect to a distal end of an endoscope uses an acoustic feedback signal.

FIG. 4 illustrate an example of an endoscopic laser lithotripsy system 400 that uses an acoustic feedback signal to control and adjust the position of an optical pathway 302 (such as a laser fiber) with respect to a distal end of an endoscope 301. The endoscope 301 may include a proximal portion and an elongate distal portion that may be configured to be inserted into a patient, such as via an orifice or incision. The endoscope 301 may be useful for providing visual inspection or treatment of soft (e.g., non-calcified) or hard (e.g., calcified) tissue as well as for visualizing or breaking up or otherwise treating kidney stones or other stones or other targets.

The lithotripsy system 400 may include or be coupled to at least one laser source 430, which may be an example of the first laser source 106 or the second laser source 116. The laser source 430 may be mechanically and optically connected to the optical pathway 302, which may include a single optical fiber or a bundle of optical fibers. The optical pathway 302 may be introduced via a proximal access port to extend within a working channel or other longitudinal passage or lumen of the endoscope 301 or similar instrument.

The endoscope 301 may include or provide visualization and illumination optics, such as a visualization optical pathway 460 and an illumination optical pathway 450, each of which may extend longitudinally along the elongate body of the endoscope 301. An eyepiece or camera or imaging display may be provided at or coupled to the visualization optical pathway 460 to permit user or machine visualization of a target region at or near a distal end of the endoscope 301. The target region may be illuminated by light 470, such as provided by an illumination light source at a proximal end of the illumination optical pathway 450 and emitted from a distal end of the illumination optical pathway 450, or may be emitted from an LED or other illumination source that may be located at or near a distal end of the endoscope, such as with electrical conductors extending longitudinally to provide power thereto.

The lithotripsy system 400 may include an actuator 485 that may actuate longitudinal translation of a distal end 304 of the optical pathway 302 within and with respect to the longitudinal passage of the endoscope 301, such as according to a control signal produced by the controller circuit 260. The controller circuit 260 may be in electrical communication with the actuator 485. The actuator 485 may be located at or near the distal end of the endoscope 301. In an example, the actuator 185 may include one or more of an electromagnetic element, an electrostatic element, a piezoelectric element, or other actuating element such as to actuate or otherwise permit longitudinal positioning of the distal end 304 of the optical pathway 302 with respect to the working channel or other longitudinal passage of the endoscope 301 or with respect to another reference location for which the endoscope 301 may serve as a frame of reference.

The lithotripsy system 400 may include the acoustic sensor 241 configured to detect an acoustic signal in response to delivery of laser energy to the target. As discussed above with reference to FIG. 2, the acoustic signal may be sensed when a laser pulse propagates through the media (e.g., liquid and vapor) along the path to the target and causes the liquid and vapor to vibrate, and when the laser pulse projects to the target and causes the target to vibrate. The acoustic sensor 241 may be located within or otherwise associated with the endoscope 301. In an example as shown in FIG. 4, the acoustic sensor 241 may be attached to a distal portion of the endoscope 301. In another example, the acoustic sensor 241 may be located at the distal end 304 of the optical pathway 302 (e.g., a laser fiber). The sensed acoustic signal may be transmitted through the optical pathway 302 to a feedback analyzer 240. In some examples, the sensed acoustic signal may additionally or alternatively be transmitted through a separate pathway different from the optical pathway 302, such as the illumination optical pathway 450, the visualization optical pathway 460, or a dedicated acoustic signal pathway.

The controller circuit 260 may adjust an irradiation parameter setting (e.g., wavelength, power, power density, pulse parameters, exposure time, total dose or energy, among others) using the one or more acoustic properties. For example, the controller circuit 260 may automatically adjust the irradiation parameter setting and/or the laser fiber position or orientation to achieve a desired acoustic signal amplitude, such as to maximize the amplitude of acoustic signal peak 355 as shown in FIG. 3B.

In some examples, the feedback analyzer 240 may generate one or more acoustic properties from the acoustic signal, and recognize the target structure as a category of calculi structure or as a category of anatomical structure (e.g., soft or hard tissue), as discussed above with reference to FIG. 2. The controller circuit 260 may adjust the irradiation parameter setting and/or the laser fiber position or orientation based on the identification of calculi target 322 as one of a plurality of calculi types with distinct compositions using the one or more acoustic properties generated from the acoustic signal, such as by using the target detector 246 and/or target classifier 248.

In some examples, the feedback analyzer 240 may calculate or estimate a distance between the distal end of the optical pathway 302 and the target (the "fiber-target distance") using one or more acoustic properties, such as temporal information about an acoustic signal peak corresponding to the laser-target interaction, as discussed above with reference to FIGS. 3A-3B. The controller circuit 260 may control the actuator 485 to adjust the position or orientation of the fiber distal end 304 based on the calculated fiber-target distance. For example, if the calculated distance exceeds a desired laser firing range (within a specified margin), then the controller circuit 260 may generate a control signal to the actuator 485 to move the optical pathway 302 longitudinally towards the target until the fiber distal end 304 reaches within a desired laser firing range relative to the target.

In some examples, the feedback analyzer 240 may receive additional feedback from the target, and using such additional feedback, together with the acoustic feedback, to perform one of more of operations including, for example, identifying target structure type, estimating the fiber-target distance, adjusting an irradiation parameter setting and controlling the laser source 430 to deliver laser energy in accordance with the adjusted irradiation parameter setting, or controlling the actuator 485 to move the distal portion of the optical pathway 302 longitudinally to achieve a desired fiber-target distance. In an example as illustrated in FIG. 4, the lithotripsy system 400 may include an endoscopic camera or imaging device 425 that may collect imaging signal reflected from the target in response to electromagnetic radiation (e.g., illumination light 470) of the target. The imaging signal may be transmitted to a feedback analyzer 240 through the optical pathway 460. Alternatively, the imaging signal reflected from the target may be transmitted through the optical pathway 302. An optical splitter may direct the reflected imaging signal to the feedback analyzer 240. The feedback analyzer 240 may include a spectrometer that may generate one or more spectroscopic properties from the imaging data. The feedback analyzer 240 may recognize the target as a calculi structure or anatomical structure, or classify the target as one type of tissue or one type of calculi of distinct composition using the one or more spectroscopic properties. The feedback analyzer 240 may calculate or estimate the fiber-target distance using the spectroscopic properties, an example of which is discussed below with reference to FIG. 5.

The controller circuit 260 may adjust irradiation parameter settings using the one or more spectroscopic properties. The controller circuit 260 may control the actuator 485 to adjust the position or orientation of the fiber distal end 304 based on the calculated distance.

In some examples, the feedback analyzer 240 may measure a laser spot size on the target from an image of the corresponding portion of the target such as taken by the endoscopic camera or imaging device 425. The laser spot size, such as a diameter or an area of a circular shaped laser spot, is correlated to the fiber-target distance. A larger spot size corresponds to a longer fiber-target distance, and a smaller spot size corresponds to a shorter fiber-target distance. Based on the laser spot size, the controller circuit 260 may generate a control signal to the actuator 485 for actuating longitudinal translation of the optical pathway 302 such as to adjust the adjust the position of the fiber distal end 304 relative to the target, such as to obtain or maintain a desired laser spot size.

Figure 5:
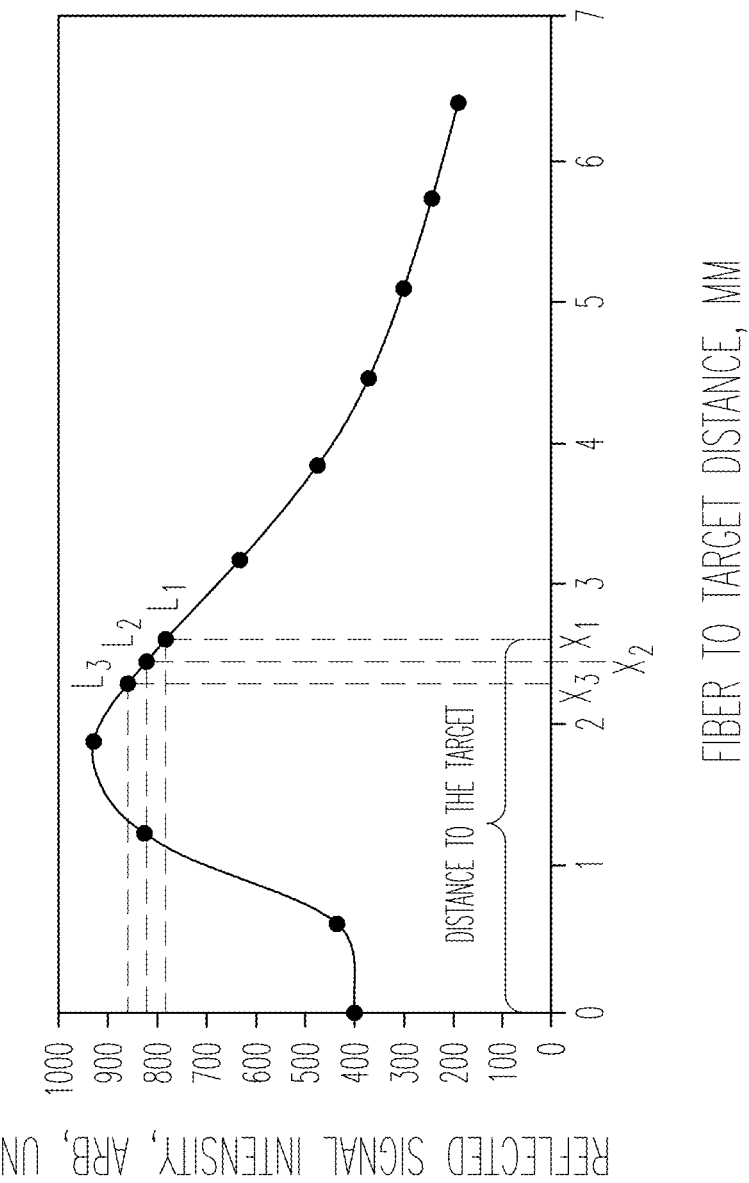
FIG. 5 illustrates an example of a calibration curve representing a relationship between a spectroscopic reflected signal intensity and the distance between a distal end of a fiber and a target structure using the feedback signal reflected from the target structure.

FIG. 5 is a diagram illustrating a calibration curve 500 representing a relationship between a spectroscopic reflected signal intensity (e.g., spectroscopic signal reflected from the target structure in response to the electromagnetic radiation) and the distance between a distal end of a fiber and a target structure (the "fiber-target distance") using the feedback signal reflected from the target structure. The calibration curve 500 may be generated by measuring the reflected light intensity at different distances between the tissue and spectroscopic probe distal end when the target structure is projected by electromagnetic radiation at a specific wavelength (e.g., 450 nm or 730 nm). By referencing the calibration curve, analyses of a spectroscopic signal allow quick estimation of the distance.

An exemplary process of generating the calibration curve is as follows. First, reference value for each distance may be calculated. The calibration curve itself may not be used for identifying the distance, because light reflection intensity depends of the reflectance of specimen or so on. One example of reference value to cancel the effect of reflectance of specimen is as follows:

$$\text{Reference value} = dI/dx * 1/I \tag{1}$$

During an in vivo surgery process, an operator may move the fiber or endoscope with continuous recording of the spectroscopic feedback until the reflection spectra of the target tissue composition may be detected.

Referring to FIG. 5, a first spectrum may be measured at distance $x_1$ where the reflected light intensity is $I_1$. At this timing, actual value of $x_1$ and curve of reflected signal intensity is unknown. Then, the fiber or endoscope distal end (reflected light detector) may be moved continually, and the next reflection light intensity $I_2$ corresponding the distance $x_2$ may be measured. $x_2$ may be close to $x_1$, such that the curve between $x_1$ and $x_2$ may be approximated as linear. At this timing, $x_1$, $x_2$ and curve of reflected signal intensity is unknown. A compared value may be calculated using $I_1$, $I_2$ and delta $(x_2-x_1)$, as follows:

$$\text{Compared value} = \text{delta}(I_2-I_1)/\text{delta}(x_2-x_1) * 1/I_1 \tag{2}$$

Then, the reference values are searched for one that is identical to the compared value. If there is only one reference value $(x_r)$ found to be identical to the compared value given in Equation (2), then $x_r$ may be determined as distance of $x_1$. If there are two reference values $(x_{r1}, x_{r2})$, then the fiber or endoscope distal end (reflected light detector) may be continued to move, and the next reflection light intensity $I_3$ corresponding the distance $x_3$ may be measured. $x_3$ may be close to $x_2$, so that the curve between $x_2$ and $x_3$ may be approximated as linear. At this timing, $x_1$, $x_2$, $x_3$ and curve of reflected signal intensity is unknown. A new compared value can be calculated as follows using $I_1$, $I_2$, $I_3$, delta $(x_2-x_1)$, and delta $(x_3-x_2)$.

$$\text{Compared value} = \text{delta}(I_3-I_2)/\text{delta}(x_3-x_2) *1/I_2 \quad (3)$$

Then, the reference values are searched for one that is identical to $x_{r1}$+delta $(x_2-x_1)$ and $x_{r2}$+delta $(x_2-x_1)$. The references values may be compared to the compared value given in Equation (3). The distance whose reference value is more similar to the compared value is estimated as actual distance.

During in vivo surgery process, an example method may comprise moving the fiber or endoscope with continuous recording of the spectroscopic feedback until the reflection spectra of the target composition will be detected. With the major case when the spectroscopic distal end is moving toward the target, the intensity of the detected reflected light initially will be weak and will be increased with reducing a distance between the target and a fiber end. For example, the first spectrum was measured on distance $d_1$ where the reflected light intensity is $I_1$. Continued slightly moving of the fiber or endoscope distal end toward the target, with continuous collecting the reflection data, and the method may measure the next reflection light intensity $I_2$ corresponding the distance $d_2$. The method may then comprise calculation of the value of reflected signal changes slope=delta $(I_2-I_1)$/delta $(d_2-d_1)$ [1]. To make the value of the calculated slope independent on the reflected light intensity the calculated slope may be normalized. The final formula to calculate slope of reflected light at measured distance becomes:

$$\text{Slope(normalized)} = [\text{delta}(I_2-I_1)/\text{delta}(d_2-d_1)]/I_0 \quad (4)$$

where: $I_0$=AVERAGE(I1,I2)

The method may then compare the calculated slope to the one on the calibration curve in a library to allow estimating the required distance. All calculation may be done fast using software.

Figure 6:
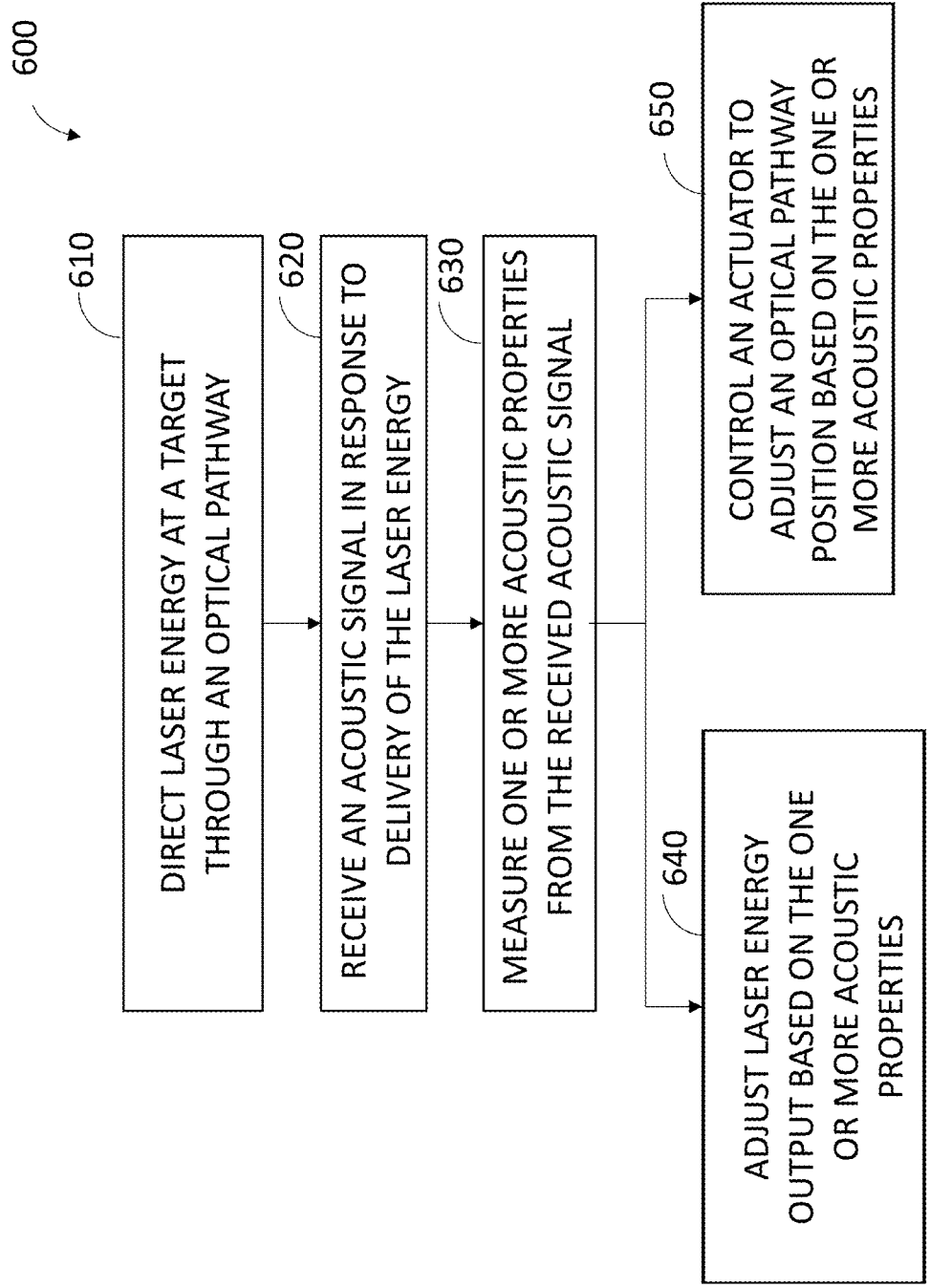
FIG. 6 is a flow chart illustrating a method for controlling a laser system to deliver a laser beam to a target structure in a body of a subject.

FIG. 6 is a flow chart illustrating a method 600 for controlling a laser system to deliver a laser beam to a target structure in a body of a subject, such as an anatomical structure (e.g., soft tissue, hard tissue, or abnormal such as cancerous tissue) or a calculi structure (e.g., kidney or pancreobiliary or gallbladder stone). The method 600 may be implemented in and executed by a laser energy delivery system, such as the laser energy delivery system 100 or a variant thereof, such as the laser feedback control system 200 or the lithotripsy system 400. Although the processes of the method 600 are drawn in one flow chart, they are not required to be performed in a particular order. In various examples, some of the processes may be performed in a different order than that illustrated herein.

At 610, laser energy (e.g., laser beams or pulses) are delivered to a target. The laser energy may be generated from a laser source such as the first laser source 106 or the second laser source 116, and transmitted through an optical pathway such as the first optical pathway 108 or the second optical pathway 118 or a variant thereof such as the signal transmission pathway 280, as discussed above with reference to FIGS. 1 and 2.

At 620, acoustic signals may be sensed in response to the delivery of laser energy. As the laser pulses propagate through the media (e.g., liquid and vapor) along the path to the target, the liquid and vapor absorb laser energy and vibrate. When the laser pulse reaches the target, the target absorbs laser energy and vibrates. The vibration of the liquid and vapor media and the vibration of the target structure produce respective pressure waves, which may be sensed as acoustic signals. An example of the acoustic signal in response to laser energy passing through the media and interacting with the target is shown in FIGS. 3A-3B. As discussed above with reference to FIG. 2, the acoustic sensor may include microphones, hydrophones, capacitive sensors, piezoelectric sensor, piezoceramic sensor, fiber-optic sensors, or solid-state acoustic detectors, among others. The acoustic sensor may be located within or otherwise associated with the endoscope, such as on a distal portion of the endoscope in an example. The acoustic sensor may alternatively be located at the distal portion of an optical pathway (e.g., a laser fiber), such as the distal end 304 of the optical pathway 302.

At 630, the acoustic signal may be analyzed to extract one or more acoustic properties. The acoustic signal may be transmitted through the same optical pathway for transmitting the laser pulses, or through a separate different pathway such as the illumination optical pathway or the visualization optical pathway, as discussed above with reference to FIG. 4. Examples of the acoustic properties may include intensity, power, frequency or spectral content, or a graphical feature or shape of the received acoustic signal. In some examples, the acoustic properties may include one or more statistical features (e.g., signal mean or variance) of the acoustic signal.

The one or more acoustic properties may be used for controlling laser energy delivery in several ways. At 640, laser energy output may be adjusted, such as via the controller circuit 260, based on one or more acoustic properties. For example, the acoustic signal intensity (e.g., amplitude) is correlated to laser power density. The controller circuit 260 may automatically adjust an irradiation parameter setting (e.g., power, power density, pulse parameters, exposure time, total dose or energy) to achieve a desired acoustic signal intensity, such as to maximize the amplitude of acoustic signal peak 355 as illustrated in FIG. 3B.

In some examples, the one or more acoustic properties may be used to identify the target type. As discussed above with reference to FIG. 2, for a tissue target or a calculi target, its ability to absorb laser energy depends on its composition and liquid content. Different target types, such as different calculi structures or soft or hard tissue, may have different composition and/or liquid content. When these targets absorb different amount of laser energy, they may produce respective different vibration patterns that may be sensed as different acoustic properties. The one or more acoustic signal properties may be used to identify the target as one of a plurality of structure categories, such as a category of calculi structure or a category of anatomical structure, such as by using the target detector 246. Additionally, the one or more acoustic signal properties may be used to classify the target as one of a plurality of structure types of the same category, such as a particular tissue type within an identified category of anatomical structure or as a particular calculi type within an identified category of calculi structure, such as by using the target classifier 248. The laser irradiation parameter setting may be adjusted based on the identified target type.

In addition to or in lieu of adjusting laser energy output, at 650, the one or more acoustic properties may be used to automatically adjust a position or orientation of a distal portion of an optical pathway (e.g., a laser fiber) for delivering laser pulses, such as to change a distance between the distal end the laser fiber and the target (the "fiber-target distance"). The adjustment may be achievement via an actuator, such as the actuator 485 as illustrated in FIG. 4, which may actuate longitudinal translation of a distal portion of the optical pathway (e.g., laser fiber) within and with respect to the longitudinal passage of the endoscope in accordance with a control signal produced by the controller circuit 260. In an example, adjustment of the position or orientation of the distal portion of an optical pathway (e.g., the distal end 304 of the optical pathway 302) may be performed along with adjustment of laser energy output (e.g., adjustment of an irradiation parameter setting) to obtain or maintain a desired acoustic signal amplitude, such as to maximize the amplitude of acoustic signal peak 355.

In some examples, the one or more acoustic properties may be used to calculate or estimate the fiber-target distance. Using the estimated fiber-target distance as a feedback signal, the laser fiber position may be adjusted such that the target is within a desired laser firing distance. One example of such an acoustic property is a time interval $(t_3-t_0)$ as illustrated in FIG. 3B, which represents laser pulse travel time from the laser fiber distal end 304 to the target 322. Such a time interval is correlated to, and may be used to estimate, the fiber-target distance. A control signal, such as generated by the controller circuit 260, may control the actuator to automatically adjust the laser fiber position such as to obtain or maintain a desired time interval $t_3-t_0$.

In some examples, additional feedback (different from the acoustic feedback) may be used to adjust laser energy output at 540, and/or to control an actuator to adjust the position or orientation of the distal end of the optical pathway. Examples of such additional feedback may include, for example, one or more spectroscopic signal properties generated from the spectroscopic signal, or one or more imaging properties generated from the imaging signal. In some examples, such additional feedback may be used to identify different target types, such as according to various examples as discussed above with reference to FIG. 2. In some examples, such additional feedback may be used to calculate or estimate the fiber-target distance, such as according to various examples as discussed above with reference to FIG. 5. The identification of the different target types and the estimated fiber-target distance may be used such as by the controller circuit 260 to controllably adjust the laser energy output at 650, and/or to controllably adjust the position of the distal portion of the optical pathway that directs the laser energy to the target.

Figure 7:
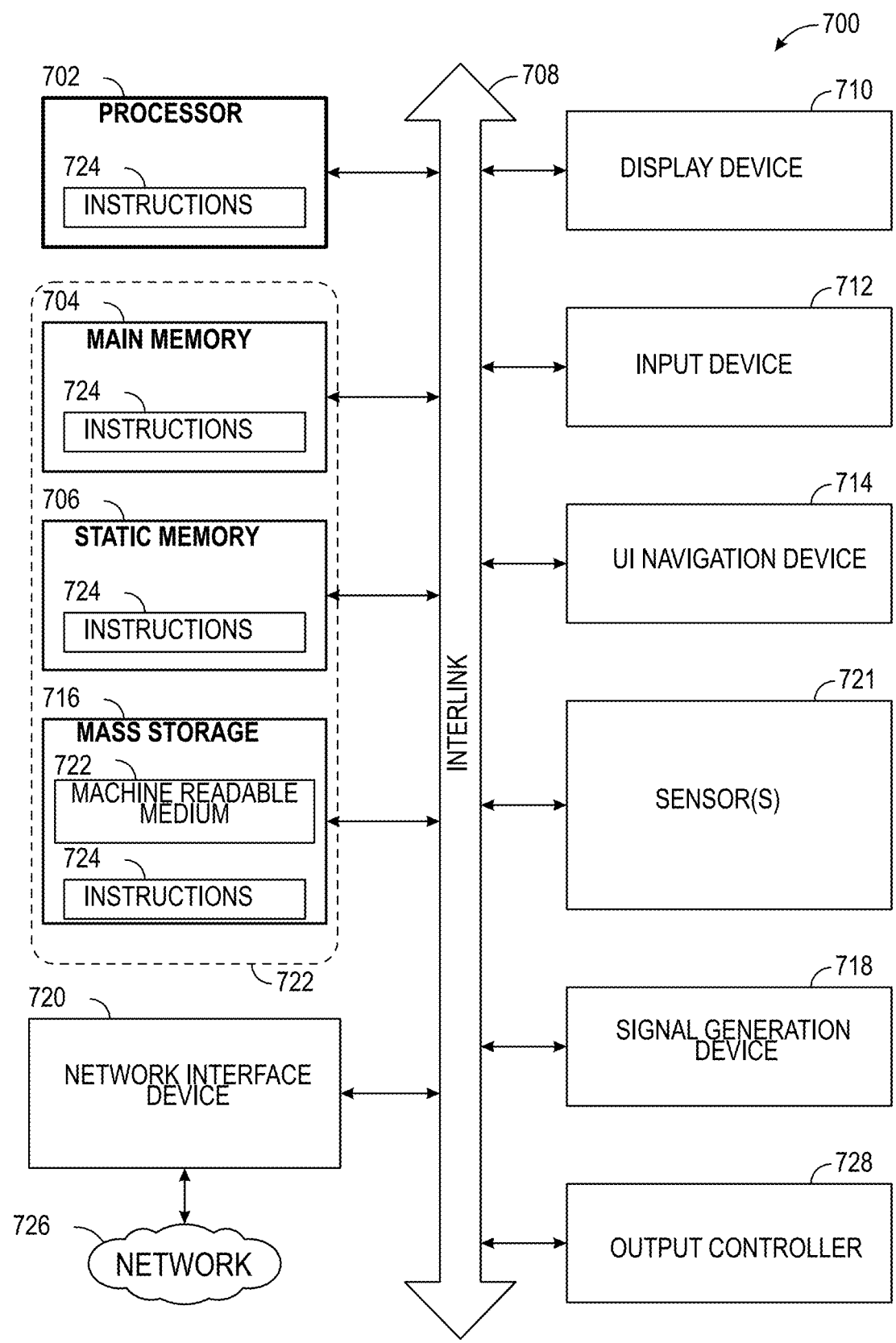
FIG. 7 is a block diagram illustrating an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the laser energy delivery system 100 (e.g., the laser feedback control system 101) or the laser feedback control system 200.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine-readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 724 may further be transmitted or received over a communication network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communication network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A endoscopic laser energy delivery system, comprising:
   a laser system configured to direct laser energy to a target in a body of a subject via an optical pathway;
   an acoustic sensor configured to sense an acoustic signal resulting from pressure waves in liquid media produced by the laser energy incident on the target; and
   an acoustic feedback controller circuit configured to:
      measure one or more acoustic properties from the sensed acoustic signal, the one or more acoustic properties including temporal information about a peak of the acoustic signal, wherein the temporal information represents time elapsed for the laser energy to travel from the laser system to target through the liquid media and time elapsed for the acoustic signal to travel to the acoustic sensor;

estimate a distance between a distal end of the optical pathway and the target based at least in part on the temporal information about the peak of the acoustic signal; and generate a first control signal for controlling the laser system to produce laser energy for delivery to the target based on the estimated distance between the distal end of the optical pathway and the target.

2. The endoscopic laser energy delivery system of claim 1, wherein:

the acoustic feedback controller circuit is configured to generate the first control signal to the laser system to adjust a laser irradiation parameter setting based on the one or more acoustic properties; and the laser system is configured to produce laser energy in accordance with the adjusted laser irradiation parameter setting.

3. The endoscopic laser energy delivery system of claim 1, wherein the acoustic sensor is configured to be attached to a distal portion of an endoscope.

4. The endoscopic laser energy delivery system of claim 1, wherein the acoustic sensor includes a piezoelectric sensor.

5. The endoscopic laser energy delivery system of claim 1, wherein the acoustic sensor includes a microphone.

6. The endoscopic laser energy delivery system of claim 1, wherein the one or more acoustic properties include an acoustic signal intensity.

7. The endoscopic laser energy delivery system of claim 1, wherein the one or more acoustic properties include an acoustic signal shape characteristic.

8. The endoscopic laser energy delivery system of claim 1, wherein the one or more acoustic properties include a frequency or spectral content of the sensed acoustic signal.

9. The endoscopic laser energy delivery system of claim 1, wherein the acoustic feedback controller circuit is configured to identify the target as one of a plurality of structure types using the measured one or more acoustic properties or one or more spectroscopic properties.

10. The endoscopic laser energy delivery system of claim 9, wherein the acoustic feedback controller circuit is configured to identify the target as one of a calculus structure or an anatomical structure using the measured one or more acoustic properties or one or more spectroscopic properties.

11. The endoscopic laser energy delivery system of claim 10, wherein the acoustic feedback controller circuit is configured to:

classify the target as one of a plurality of calculi types with respective distinct compositions using the measured one or more acoustic properties or one or more spectroscopic properties; and generate the first control signal to the laser system to adjust a laser irradiation parameter setting based on the classification of the target, and to deliver laser energy to the target of the classified calculus type in accordance with the adjusted laser irradiation parameter setting.

12. The endoscopic laser energy delivery system of claim 10, wherein the acoustic feedback controller circuit is configured to:

classify the target as one of a plurality of tissue types using the measured one or more acoustic properties or one or more spectroscopic properties; and generate the first control signal to the laser system to deliver, or withhold delivery of, laser energy in accordance with the classified tissue type.

13. The endoscopic laser energy delivery system of claim 12, wherein the acoustic feedback controller circuit is configured to classify the target as a treatment area or a non-treatment area, and to generate the first control signal to the laser system to deliver laser energy to the treatment area, and to withhold delivery of laser energy to the non-treatment area.

14. The endoscopic laser energy delivery system of claim 13, wherein the acoustic feedback controller circuit is configured to classify the target as normal tissue or cancerous tissue, and to generate the first control signal to the laser system to deliver laser energy to the target of the classified cancerous tissue, and to withhold delivery of laser energy if the target is classified as normal tissue.

15. The endoscopic laser energy delivery system of claim 1, comprising an optical pathway having a distal portion configured to be inserted into the subject via a longitudinal passage of an endoscope.

16. The endoscopic laser energy delivery system of claim 15, wherein the optical pathway includes a laser fiber coupled to the laser system and configured to transmit laser energy to the target.

17. The endoscopic laser energy delivery system of claim 16, wherein the optical pathway is configured to transmit the acoustic signal to the acoustic feedback controller circuit.

18. The endoscopic laser energy delivery system of claim 15, comprising an actuator configured to actuate a longitudinal translation of the optical pathway with respect to the longitudinal passage of an endoscope according to a second control signal generated by the acoustic feedback controller circuit based on the one or more acoustic properties or one or more spectroscopic properties, the longitudinal translation causing a change in position of the distal end of the optical pathway relative to the target.

19. The endoscopic laser energy delivery system of claim 18, wherein the acoustic feedback controller circuit is configured to:

generate the second control signal for actuating longitudinal translation of the optical pathway based on the estimated distance between the distal end of the optical pathway and the target.

20. The endoscopic laser energy delivery system of claim 18, wherein the acoustic feedback controller circuit is configured to:

measure a laser spot size on the target from an image of the target in response to the delivery of laser energy to the target; and generate the second control signal for actuating longitudinal translation of the optical pathway to achieve a desired laser spot size on the target.

21. A method for controlling a laser system to deliver laser energy to a target in a body of a subject, the method comprising:

directing laser energy produced by the laser system to the target via an optical pathway;

receiving, via an acoustic sensor, an acoustic signal resulting from pressure waves in liquid media produced by the laser energy incident on the target;

measuring, via an acoustic feedback controller circuit, one or more acoustic properties from the received acoustic signal, the one or more acoustic properties including temporal information about a peak of the acoustic signal, wherein the temporal information represents time elapsed for the laser energy to travel from the laser system to target through the liquid media and time elapsed for the acoustic signal to travel to the acoustic sensor;

estimating a distance between a distal end of the optical pathway and the target based at least in part on the temporal information about the peak of the acoustic signal; and generating, via the acoustic feedback controller circuit, a first control signal for controlling the laser system to produce laser energy for delivery to the target based on the estimated distance between the distal end of the optical pathway and the target.

22. The method of claim 21, comprising generating the first control signal to adjust a laser irradiation parameter setting based on the one or more acoustic properties, and producing laser energy in accordance with the adjusted laser irradiation parameter setting.

23. The method of claim 21, wherein the one or more acoustic properties include one or more of an acoustic signal intensity, an acoustic signal shape characteristic, or a frequency or spectral content of the received acoustic signal.

24. The method of claim 21, further comprising identifying the target as one of a plurality of structure types using the measured one or more acoustic properties or one or more spectroscopic properties, the plurality of structure types including one of a calculus structure or an anatomical structure.

25. The method of claim 24, further comprising:

classifying the target as one of a plurality of calculi types with respective distinct compositions using the measured one or more acoustic properties or one or more spectroscopic properties;

adjusting a laser irradiation parameter setting for the laser system based on the classification of the target; and generating the first control signal to the laser system to deliver laser energy to the target in accordance with the adjusted laser parameter setting.

26. The method of claim 24, further comprising:

classifying the target as one of a plurality of tissue types using the measured one or more acoustic properties or one or more spectroscopic properties; and generating the first control signal to the laser system to deliver, or withhold delivery of, laser energy in accordance with the classified tissue type.

27. The method of claim 21, further comprising adjusting, via an actuator, a position of the distal end of the optical pathway relative to the target based on one or more acoustic properties or one or more spectroscopic properties.

28. The method of claim 27, wherein adjusting the distal end position comprises generating, via the acoustic feedback controller circuit, a second control signal to the actuator to actuate a longitudinal translation of the optical pathway with respect to a longitudinal passage of an endoscope.

29. The method of claim 27, comprising:

measuring a laser spot size on the target from an image of the target in response to the delivery of laser energy to the target; and adjusting, via the actuator, the position of the distal end of the optical pathway to achieve a desired laser spot size on the target.

* * * * *

UNITED STATES PATENT AND TRADEMARK OFFICE
CERTIFICATE OF CORRECTION

PATENT NO. : 12,357,382 B2
APPLICATION NO. : 17/378459
DATED : July 15, 2025
INVENTOR(S) : Polejaev et al.

Page 1 of 1

It is certified that error appears in the above-identified patent and that said Letters Patent is hereby corrected as shown below:

In the Claims

In Column 28, Lines 11-12, in Claim 14, delete "claim 13," and insert --claim 12,-- therefor Signed and Sealed this
Ninth Day of September, 2025

Coke Morgan Stewart
*Acting Director of the United States Patent and Trademark Office*